(12) United States Patent
Li et al.

(10) Patent No.: US 12,070,443 B2
(45) Date of Patent: *Aug. 27, 2024

(54) METHODS OF TREATING AND PREVENTING BREAST CANCER WITH S-EQUOL

(71) Applicant: The Board of Regents of the University of Texas System, Austin, TX (US)

(72) Inventors: Rong Li, San Antonio, TX (US); Bin Yuan, San Antonio, TX (US); Tyler Curiel, San Antonio, TX (US)

(73) Assignee: The Board of Regents of the University of Texas System, Austin, TX (US)

(*) Notice: Subject to any disclaimer, the term of this patent is extended or adjusted under 35 U.S.C. 154(b) by 103 days.

This patent is subject to a terminal disclaimer.

(21) Appl. No.: 17/372,352

(22) Filed: Jul. 9, 2021

(65) Prior Publication Data

US 2021/0338632 A1 Nov. 4, 2021

Related U.S. Application Data

(63) Continuation of application No. 16/384,417, filed on Apr. 15, 2019, now Pat. No. 11,090,286.

(60) Provisional application No. 62/685,392, filed on Jun. 15, 2018.

(51) Int. Cl.
| | | |
|---|---|---|
| *A61K 31/353* | (2006.01) | |
| *A61K 39/395* | (2006.01) | |
| *A61P 35/00* | (2006.01) | |
| *C07K 16/28* | (2006.01) | |

(52) U.S. Cl.
CPC ........ *A61K 31/353* (2013.01); *A61K 39/3955* (2013.01); *A61P 35/00* (2018.01); *C07K 16/2818* (2013.01); *C07K 16/2827* (2013.01); *C07K 2317/21* (2013.01); *C07K 2317/24* (2013.01)

(58) Field of Classification Search
CPC .............................. A61K 31/352; A61P 35/00
See application file for complete search history.

(56) References Cited

U.S. PATENT DOCUMENTS

| | | | |
|---|---|---|---|
| 9,827,309 B2 | 11/2017 | Strack et al. | |
| 10,945,990 B2 | 3/2021 | Matsui et al. | |
| 11,090,286 B2 * | 8/2021 | Li | A61K 31/353 |
| 11,324,822 B2 | 5/2022 | Goodenow et al. | |
| 11,547,705 B2 | 1/2023 | Denker et al. | |
| 2005/0245492 A1 | 11/2005 | Lephart et al. | |
| 2007/0166414 A1 | 7/2007 | Constantinou | |
| 2010/0076071 A1 | 3/2010 | Lephart et al. | |
| 2016/0102070 A1 * | 4/2016 | Jackson | C07D 311/04 |
| | | | 549/406 |

FOREIGN PATENT DOCUMENTS

| | | | | |
|---|---|---|---|---|
| JP | 2007534751 A | 11/2007 | | |
| JP | 2013-126374 A | 6/2013 | | |
| JP | 2014233259 A | 12/2014 | | |
| JP | 2016-528286 A | 9/2016 | | |
| JP | 2018-508516 A | 3/2018 | | |
| JP | 2018-508593 A | 3/2018 | | |
| JP | 2018-512391 A | 5/2018 | | |
| WO | WO-2004009035 A2 * | 1/2004 | ............ | A23L 33/10 |
| WO | 2011108699 A1 | 9/2011 | | |
| WO | 2012033150 A1 | 3/2012 | | |
| WO | 2015069770 A1 | 5/2015 | | |
| WO | 2017004092 A1 | 1/2017 | | |
| WO | 2017017624 A1 | 2/2017 | | |
| WO | 2017176965 A1 | 10/2017 | | |

OTHER PUBLICATIONS

Yuan et al (Oncotarget vol. 7 pp. 42585-42497. Published Online Jun. 14, 2016) (Year: 2016).*
Clinical Trial NCT02352025. Published on Jan. 30, 2015. (Year: 2015).*
Wang et al (FASEB J vol. 32 pp. 1537-1549. Published online Nov. 16, 2017) (Year: 2017).*
Dirix (Breast Cancer Research Treatment vol. 167 pp. 671-686. Published online Oct. 23, 2017) (Year: 2017).*
Melero, I., et al., "Evolving synergistic combinations of targeted immunotherapies to combat cancer," Nature Reviews Cancer, vol. 15 (2015) pp. 457-472.
"History of changes for study: NCT02352025, S-equol in women with triple negative breast cancer," ClinicalTrials.gov archive, v6, Apr. 2018, https://clinicaltrials.gov/ct2/history/NCT02352025?V_6=View#StudyPageTop, retrieved Jan. 20, 2023, 9 pages.
Office Action in Japanese patent application No. JP2020-570066 mailed Jan. 31, 2023 (with English translation), 14 pages.
Office Action in Japanese patent application No. JP2021-522423 mailed Jan. 31, 2023 (with English translation), 7 pages.
Altin, J.G. and Sloan, E.K. The role of CD45 and CD45-associated molecules in T cell activation. Immunol. Cell Biol. 75(5):430-445 (1997).
Baum M., Buzdar A.U., Cuzick J., et al. Anastrozole alone or in combination with tamoxifen versus tamoxifen alone for adjuvant treatment of postmenopausal women with early breast cancer: first results of the ATAC randomized trial. The Lancet. 359: 2131-2139 (2002).

(Continued)

*Primary Examiner* — Theodore R. Howell
*Assistant Examiner* — George W Kosturko
(74) *Attorney, Agent, or Firm* — ROTHWELL, FIGG, ERNST & MANBECK, P.C.

(57) ABSTRACT

The present invention provides methods and compositions for treating or preventing breast cancer with S-equol. The method and compositions are particularly suited to treating triple-negative breast cancer. The S-equol may be administered alone or in combination with one or more cytotoxic or immunotherapeutic compound or molecule.

19 Claims, 20 Drawing Sheets
(17 of 20 Drawing Sheet(s) Filed in Color)

(56) References Cited

OTHER PUBLICATIONS

Beelen K., Zwart W., Linn S.C. Can predictive biomarkers in breast cancer guide adjuvant endocrine therapy? Nat Rev Clin Oncol. 9: 529-541 (2012).
Brahmer, J. R. et al. Safety and activity of anti-PD-L1 antibody in patients with advanced cancer. N Engl J Med 366 (26), 2455-2465, doi:10.1056/NEJMoal200694 (2012).
Brower, V. Checkpoint blockade immunotherapy for cancer comes of age. J Natl Cancer Inst 107(3), doi: 10.1093/jnci/djv069 (2015).
Chen, L. & Flies, D. B. Molecular mechanisms of T cell co-stimulation and co-inhibition. Nat Rev Immunol 13(4), 227-242, dol:10.1038/nr13405 (2013).
Chia, K. & Tutt, A. Triple-negative breast cancer: An update. Adv Breast Cancer 4, 75-80 (2007).
Cho, J. L., Allanson, M. & Reeve, V. E. Oestrogen receptor-beta signalling protects against transplanted skin tumour growth in the mouse. Photochem Photobiol Sci 9, 608-614, doi: 10.1039/b9pp00168a (2010).
Clark C.A., et al. Tumor-Intrinsic PD-L1 Signals Regulate Cell Growth, Pathogenesis, and Autophagy in Ovarian Cancer and Melanoma, Cancer Res. Dec. 1, 2016;76(23):6964-6974.
Clarke R. et al. Antiestrogen resistance in breast cancer and the role of estrogen receptor signaling. Oncogene. 22:7316-7339 (2003).
Cleator, S. et al. Triple-negative breast cancer: therapeutic options. Lancet Oncol. 8, 235-244 (2007).
Coates et al. Tailoring therapies—improving the management of early breast cancer: St. Gallen International Expert Consensus on the Primary Therapy of Early Breast Cancer 2015, Annals of Oncology 26(8): 1533-46 (2015).
Curiel, T. J. et al. Blockade of B7-HI improves myeloid dendritic cell-mediated antitumor immunity. Nat Med 9, 562-567, doi:10.1038/nm663 (2003).
Davies C., et al. Long-term effects of continuing adjuvant tamoxifen to 10 years versus stopping at 5 years after diagnosis of estrogen receptor-positive breast cancer: ATLAS, a randomised trial. Lancet. 381: 805-816 (2013).
Dawood, S. & Rugo, H. S. Targeting the host immune system: PD-1 and PD-L1 antibodies and breast cancer. Curr Opin Support Palliat Care 10, 336-342, doi:10.1097/SPC.0000000000000243 (2016).
Dent, R. et al. Triple-negative breast cancer: clinical features and patterns ofrecurrence. Clin Cancer Res. 13, 4429-4434 (2007).
Deroo B.J., & Korach, K.S. Estrogen receptors and human disease. J Clin Invest. 116: 561-570 (2006).
Deroo B.J., et al. Minireview: Estrogen receptor-beta: mechanistic insights from recent studies. Mol Endocrinol. 24(9): 1703-1714 (2010).
Diaz, L. K., et al. Triple negative breast carcinoma and the basal phenotype: From expression profiling to clinical practice. Advances in Anatomic Pathology 14(6), 419-430 (2007).
Dirix, L. Y., et al. Avelumab (MSB0010718C), an anti-PD-LI antibody, in patients with locally advanced or metastatic breast cancer: A phase Ib JAVELIN solid tumor trial. 2015 San Antonio Breast Cancer Symposium Abstract SI-04 (2015), 1 page.
Emens, L. A., et al. Inhibition of PD-L1 by MPDL3280A leads to clinical activity in patients with metastatic triple-negative breast cancer (TNBC). The American Association for Cancer Research Annual Meeting Abstract 2859 (2015), 1 page.
Gerson, R., et al. Recurrence and survival rates in early breast cancer cases with triple negative immunophenotype. Gae Med Mex 144, Abstract (2008), 2 pages.
Gonzalez-Angulo, A. M. Advances in triple receptor-negative breast cancer. Clin Adv Hernatol Oncol 5(12):956-957 (2007).
Goss P.E., et al. Randomized trial of letrozole following tamoxifen as extended adjuvant therapy in receptor-positive breast cancer: updated findings from NCIC CTG MA. 17. J Natl Cancer Inst. 97(17): 1262-1271 (2005).
Gupta, H. B. et al. Tumor cell-intrinsic PD-L1 promotes tumor-initiating cell generation and functions in melanoma and ovarian cancer, Signal Transduction and Targeted Therapy 1 (2016) 16030.

Haffty, B. G. et al. Locoregional relapse and distant metastasis in conservatively managed triple negative early-stage breast cancer. J Clin Oncol. 24, 5652-5657 (2006).
Harris, H.A. Estrogen receptor-beta: recent lessons from in vivo studies. Mol Endocrinol. 21: 1-13 (2007).
Hartman J., et al. Estrogen receptor beta in breast cancer-diagnostic and therapeutic implications. Steroids. 74: 635-641 (2009).
Heldring N., et al. Estrogen receptors: how do they signal and what are their targets. Physiol Rev. 87: 905-931 (2007).
Hodi, F. S. et al. Improved survival with ipilimumab in patients with metastatic melanoma. N Engl J Med 363(8), 711-723, doi:10.1056/NEJMoal003466 (2010).
Honma N., et al. Clinical importance of estrogen receptor-beta evaluation in breast cancer patients treated with adjuvant tamoxifen therapy. J Clin Oncol. 26(22): 3727-3734 (2008).
Irvin, W. J. J. & Carey, L.A. What is triple-negative breast cancer? Eur J Cancer. 44, 2799-2805 (2008).
Jackson R.L., et al. Emerging evidence of the health benefits of S-equol, an estrogen receptor beta agonist. Nutr Rev. 69(8): 432-448 (2011).
Jackson R.L., et al. Single-dose and steady-state pharmacokinetic studies of S-equol, a potent nonhormonal, estrogen receptor beta-agonist being developed for the treatment of menopausal symptoms. Menopause: The Journal of The North American Menopause Society, 18(2), 9 pages, 2010.
Jenks et al., A pilot study on the effects of S-equol compared to soy isoflavones on menopausal hot flash frequency, Journal of Women's Health, 21(6):674-682 (2012).
Kang, S. P., et al. Triple negative breast cancer: current understanding of biology and treatment options. Curr Opin Obstet Gynecol. 20: 40-46 (2008).
Kaplan, H. G. & Malmgren, J. A. Impact of triple negative phenotype on breast cancer prognosis. The Breast Journal 14:456-463 (2008).
Katzenellenbogen B., & Katzenellenbogen J. Estrogen receptor transcription and transactivation: Estrogen receptor alpha and estrogen receptor beta: regulation by selective estrogen receptor modulators and importance in breast cancer. Breast Cancer Res. 2: 335-344, (2000).
Kaufman, H. L. et al. The Society for Immunotherapy of cancer consensus statement on tumour immunotherapy for the treatment of cutaneous melanoma. Nat Rev Clin Oncol 10, 588-598,doi: 10.1038/nrclinonc.2013.153 (2013).
Kittaneh, M., et al. Molecular profiling for breast cancer: A comprehensive review, Biomark Cancer 5:61-70, (2013).
Krege, J. H. et al. Generation and reproductive phenotypes of mice lacking estrogen receptor beta. Proc Natl Acad Sci USA 95:15677-15682 (1998).
Lin, P. Y. et al. B7-H1-dependent sex-related differences in tumor immunity and immunotherapy responses. J Immunol 185(5):2747-2753, doi:I0.4049/jimmunol.1000496 (2010).
Marotti, J. D., et al. Estrogen receptor-beta expression in invasive breast cancer in relation to molecular phenotype: results from the Nurses' Health Study. Modern Pathology 23(2), 197-204, doi:I0.1038/modpathol.2009. 158 (2010).
Marzagalli M., et al. Estrogen Receptorβ in Melanoma: From Molecular Insights to Potential Clinical Utility, Frontiers in Endocrinology, vol. 7, Article 140 (2016).
McDonnell D., & Norris J. Connections and regulation of the human estrogen receptor. Science. 296:1642-1644 (2002).
Mellman, I., et al. Cancer immunotherapy comes of age. Nature 480, 480-489, doi:I0.1038/naturel0673 (2011).
Murphy L.C., & Watson P.H. Is oestrogen receptor-beta a predictor of endocrine therapy responsiveness in human breast cancer? Endocr Relat Cancer. 13:327-334 (2006).
Nanda, R. et al. Pembrolizumab in patients with advanced triple-negative breast cancer: Phase Ib KEYNOTE-012 Study. J Clin Oncol 34, 2460-2467, doi:I0.1200/JC0.2015.64.8931 (2016).
Padrón Á, et al. Age effects of distinct immune checkpoint blockade treatments in a mouse melanoma model, Exp Gerontol. May 2018;105:146-154.

(56) References Cited

OTHER PUBLICATIONS

Li, Y., et al. Post-mastectomy radiotherpay for breast cancer pateitns with T1-T2 and 1-3 positive lymph nodes: a meta analysis, PLOS ONE 8(12), 2013, 9 pages.
Pardoll, D. & Drake, C. Immunotherapy earns its spot in the ranks of cancer therapy. J Exp Med 209, 201-209, dol: I0.1084/jem.20112275 (2012).
Pardoll, D. M. The blockade of immune checkpoints in cancer immunotherapy. Nat Rev Cancer 12, 252-264, doi:10.1038/nrc3239 (2012).
Pfefferle, A. D. et al. Transcriptomic classification of genetically engineered mouse models of breast cancer identifies human subtype counterparts. Genome Biol 14, R125, doi:10.1186/gb-2013-14-11-r125 (2013).
Reese, J.M. et al. ERβ1: characterization, prognosis, and evaluation of treatment strategies in ER alpha positive and—negative breast cancer. BMC Cancer 14, 749, doi:I0.1186/1471-2407-14-749 (2014).
Reis-Filho, J. S. & Tutt, A. N. J. Triple negative tumours: A critical review. Histopathology 52, 108-118 (2008).
Ribas, A. and Wolchok, J.D. Cancer immunotherapy using checkpoint blockade. Science 359:1350-1355 (2018).
Rugo, H. S. et al. Preliminary efficacy and safety of pembrolizumab (MK-3475) in patients with PD-LI-positive, estrogen receptor-positive (ER+ )/HER2-negative advanced breast cancer enrolled in KEYNOTE-028. 2015 San Antonio Breast Cancer Symposium Abstract S5-07 (2016), 2 pages.
Sachs, J.R. et al. Optimal dosing for targeted therapies in oncology: drug development cases leading by example. Clin. Cancer Res. 22(6):OF1-7 (2016).
Sahin, U. and Tureci, O. Personalized vaccines for cancer immunotherapy. Science 359:1355-1360 (2018).
Santen R.J., et al. History of aromatase: saga of an important biological mediator and therapeutic target. Endocr Rev. 30: 343-375 (2009).
Schwen, R.J., et al. Elucidation of the metabolic pathway of S-equol in rat, monkey and man. Food Chemistry Toxicology. 50: 2074-2083 (2012).
Setchell, K.D., et al. S-equol, a potent ligand for estrogen receptor beta, is the exclusive enantiomeric form of the soy isoflavone metabolite produced by human intestinal bacterial flora. Am J Clini Nutr. 81: 1072-1079 (2005).
Setchell, K.D., et al. The clinical inportance of the metabolite equol-a clue to the effectiveness of soy and its isoflavones. Nature. 132:3577-3584 (2002).
Shaaban A.M., et al. Nuclear and cytoplasmic expression of ERbeta1, ERbeta2, and ERbeta5 identifies distinct prognostic outcome for breast cancer patients. Clin Cancer Res. 14: 5228-5235 (2008).
Sharma, P. & Allison, J. P. Immune checkpoint targeting in cancer therapy: towards combination strategies with curative potential. Cell 161, 205-214, doi:I0.1016/j.cell.2015.03.030 (2015).
Shou, J., et al. Mechanisms of tamoxifen resistance: increased estrogen receptor-HER2/neu cross-talk in ER/HER2-positive breast cancer. J Natl Cancer Inst. 96(12): 926-935 (2004).
Smith, I.E., et al. Neoadjuvant treatment of postmenopausal breast cancer with anastrozole, tamoxifen, or both in combination: The immediate preoperative anastrozole, tamoxifen, or combined with tamoxifen (IMPACT) multicenter double-blind randomized trial. J Clini Onc. 23(22): 5108-5116 (2005).
Smith C.L., & O'Malley B.W. Coregulator Function: A Key to Understanding Tissue Specificity of Selective Receptor Modulators. Endocrine Reviews 25(1):45-71 (2004).
Steinberg S.M., et al. Myeloid Cells That Impair Immunotherapy Are Restored in Melanomas with Acquired Resistance to BRAF Inhibitors, Cancer Res. Apr. 1, 2017;77(7):1599-1610.
Thomas, C., & Gustafsson, J.A. The different roles of ER subtypes in cancer biology and therapy. Nat Rev Cancer. 11: 597-608 (2011).
Topalian, S. L., et al. Immune checkpoint blockade: a common denominator approach to cancer therapy. Cancer Cel 27, 450-461, doi:I0.1016/j.ccell.2015.03.001 (2015).

Topalian, S. L. et al. Survival, durable tumor remission, and long-term safety in patients with advanced melanoma receiving nivolumab. J Clin Oncol 32(10), 1020-1030, doi:I0.1200/JC0.2013.53.0105 (2014).
Topalian, S. L., et al. Targeting the PD-1/B7-H1 (PD-L1) pathway to activate anti-tumor immunity. Curr Opin Immunol 24, 207-212, doi:I0.1016/j.col.2011.12.009 (2012).
Urruticoechea, A., et al. Proliferation marker Ki-67 in early breast cancer. Journal of Clinical Oncology 23:7212-7220 (2005).
Usui et al. Effects of natural S-equol supplements on overweight or obesity and metabolic syndrome in the Japanese, based on sex and equol status, Clinical Endocrinology, 78:365-372 (2013).
Wolchok, J. D. et al. Safety and clinical activity of combined PD-1 (nivolumab) and CTLA-4 (ipilimumab) blockade in advanced melanoma patients. N Engl J Med 369, 122-133, doi:I0.1056/NEJMoa1302369 (2013).
Yao et al., Potentiation of brain mitochondrial function by S-equol and R/S-equol estrogen receptor beta-selective phytoSERM treatments, Brain Research, 1514:128-141 (2013).
Yuan, B. et al. A phosphotyrosine switch determines the antitumor activity of ERbeta. J Clin Invest 124, 3378-3390, doi:10.1172/JCI74085 (2014).
Yuan, B. et al. Tyrosine phosphorylation regulates ERbeta ubiquitination, protein turnover, and inhibition of breast cancer. Oncotarget 7(27): 42585-42597, doi: 10.18632/oncotarget.10018 (2016).
Zhao et al., A select combination of clinically relevant phytoestrogens enhances estrogen receptor β-binding selectivity and neuroprotective activities in vitro and in vivo. Endocrinology, 150(2):770-783 (2009).
International Search Report and Written Opinion for PCT/US2019/027505 dated Jul. 26, 2019, 13 pages.
Widyarini, S., et al., Protective effect of the isoflavonoid equol against hairless mouse skin carcinogenesis induced by UV radiation alone or with a chemical cocarcinogen, Photochemistry and Photobiology, 2005, 81:32-37.
Schwen, R. J., et al. Toxicokinetics and lack of uterotropic effect of orally administered S-equol, Food and Chemistry Toxicology 50 (2012) 1741-1748.
Rugo, H. S., et al. Safety and antitumor activity of pembrolizumab in patients with estrogen receptor-positive/human epidermal growth factor receptor 2-negative advanced breast cancer, Clin Cancer Res 24(12), 2018, 9 pages.
Magee, P. J., et al., "Daidzein, R-(+)equol and S-(-)equol inhibit the invasion of MDA-MB-231 breast cancer cells potentially via the down-regulation of matrix metalloproteinase-2," Eur J Nutr (2014) 53:345-350.
International Search Report issued for PCT/US2019/027485 mailed Sep. 3, 2019, 6 pages.
Prevention. Medical Dictionary. Published 2020 (Year: 2020).
Yuan (Oncotarget vol. 7 pp. 42585-42598 published online Jun. 14, 2016) (Year:2016).
Wang (FASEB J vol. 3 pp. 1537-1549. Published online Nov. 16, 2017) (Year: 2017).
Dua (Ajho vol. 13 pp. 20-27. Published 2017). (Year: 2017).
BIOCOMPARE Anti-PD-1 and Anti-PD-L1 antibodies (Year: 2018).
NCT02352025 published on Jan. 30, 2015 (Year: 2015).
ECACC (European Collection of Authenticated Cell Cultures published 2017) (Year: 2017).
Skalniak et al., Oncotarget vol. 8 pp. 72167-72181. Published online Aug. 7, 2017 (Year: 2017).
MDA-MB-231 Cell line information page. ECACC (European Collection of Authenticated Cell Cultures published 2017) (Year: 2017).
Clinical Trial NCT02352025. Made available to the publich on Jan. 30, 2015. (Year: 2015).
Office Action for Indian application No. 202117010284 dated Aug. 23, 2022, English translation, 5 pages.
ClinicalTrials.gov Identifier: NCT00998920 (post Oct. 21, 2009), 7 pages.
Nonacs, R., "What is S-Equol? Does it really work for menopausal symptoms?," womensmentalheal.org, Mar. 13, 2015, 2 pages.
BioXcell, InVivoMab anti-mouse PD-1 (CD279), clone RMP1-14, catalog No. BE0146 printed Feb. 11, 2022, 14 pages.

(56) References Cited

OTHER PUBLICATIONS

Examination Report issued for Australian Patent Application No. 2019285640 on May 24, 2024, 4 pages.

* cited by examiner

α-PD-1: 200 μg/mice every 3 days;
S-equol: 50 mg/kg/day.

METHODS OF TREATING AND PREVENTING BREAST CANCER WITH S-EQUOL

CROSS-REFERENCE TO RELATED APPLICATIONS

This application is a continuation of U.S. application Ser. No. 16/384,417 filed Apr. 15, 2019, which claims priority from U.S. Provisional Application Ser. No. 62/685,392, filed Jun. 15, 2018, which is hereby incorporated by reference in its entirety.

STATEMENT OF GOVERNMENTAL SUPPORT

This invention was made with U.S. Government support under grant number CA206529 awarded by the National Institutes of Health and the Texas Cancer Research Grant Contract under grant number DP150055 by the Cancer Prevention and Research Institute of Texas. The U.S. Government and the Texas State Government have certain rights in this invention.

BACKGROUND OF THE INVENTION

Field of the Invention

This invention relates to methods and compositions for treating or preventing breast cancer with a pharmaceutically effective amount of S-equol or a pharmaceutical composition comprising S-equol. In a preferred embodiment, the invention relates to the treatment of triple-negative breast cancer. In another embodiment, the method relates to a combination therapy using S-equol and another anti-cancer treatment, such as immunotherapy.

Description of the Related Art

Breast cancer is highly heterogeneous and consists of multiple subtypes. Triple negative breast cancer (TNBC) is a subtype of breast cancer that lacks the expression of estrogen receptor α (ERα), progesterone receptor (PR), and human epidermal growth factor receptor 2 (HER2). (Cleator et al. (2007); Kang et al. (2008); Chia and Tutt (2007); Diaz et al. (2007); Gonzalez-Angulo (2007); Reis-Filho and Tutt (2008); Irvin and Carey (2008)). While TNBC constitutes approximately 15% of all breast cancers, mortality of patients with TNBC is disproportionately higher than those with other subtypes of breast cancer. TNBC tends to have more rapid disease progression (Gerson et al. (2008); Dent et al. (2007); Haffty et al. (2006); Kaplan and Malmgren (2008)), yet the "triple negative" characteristic excludes TNBC patients from the benefit of standard hormonal and HER2-targeted therapies (Baum et al. (2002); Davies et al. (2013); Goss et al. (2005); Santen et al. (2009); Shou et al. (2004); Smith et al. (2005)). Despite several prospects on the therapeutic horizon for TNBC, chemotherapy remains the only standard treatment for TNBC patients. Those who are resistant to current chemotherapies suffer from unnecessary toxicity without substantial clinical benefits. Therefore, there is an urgent need to develop safer and more effective treatment for TNBC.

Recent years have witnessed major clinical breakthroughs in cancer immunotherapies (Mellman et al. (2011); Kaufman et al. (2013); Brower (2015); Topalian et al. (2015)), which include blocking the immune-suppressive immune checkpoint molecules CTLA-4 (cytotoxic T-lymphocyte-associated protein 4 or CD152 [cluster of differentiation 152]), PD-1 (programmed cell death protein 1), and PD-L1 (programmed death ligand 1; Hodi et al. (2010); Wolchok et al. (2013); Topalian et al. (2014)). PD-1 is a checkpoint protein on T-cells that serves as an "off switch" to keep T cells from attacking other cells in the body. PD-1 interacts with PD-L1 on tumor cells. When PD-L1 interacts with PD-1, it prevents the T-cells from attacking the tumor cells. PD-1 inhibitors are currently being used to treat certain cancers.

A review of cancer immunotherapy using checkpoint blockade has been published as in Ribas and Wolchok, (2018) (see reference list herein), and is incorporated by reference herein in its entirety, particularly for the purposes of discussing pathways to be targeted with immunotherapy and antibodies for use in that checkpoint blockade. In addition, methods of rationally selecting cancer vaccine targets based on a patient's "mutanome," namely, a set of somatic mutations that generate cancer-specific neoepitopes which can be recognized by autologous T cells as foreign, are discussed in Sahin and Tureci, (2018) (see reference list herein). This publication is also incorporated by reference herein in its entirety for discussing personalized targeting of tumor antigens such that cells of the immune system (e.g., CD4+T helper cells and CD8+T cytotoxic cells) can be activated to attack tumor cells. See, FIGS. 10 and 11. Both of these types of cancer immunotherapy can be combined with the use of S-equol in accordance with the present invention.

$CD4^+$ T cells play a key role in the functioning of a healthy immune system. They assist B cells to make antibodies, activate the microbe killing capacity of macrophages and recruit other immune cells to infected or inflamed areas of the body. These activities are orchestrated through their production of various cytokines and chemokines. It has been known for some time that uncommitted CD4+ T-cells can differentiate into Th1 or Th2 cells, based on the prevailing pro-inflammatory/anti-inflammatory environment, and that these activated Th1 and Th2 cells had distinct cytokine production patterns and functions. Generally, Th1 cells were associated with the eradication of intracellular pathogens whereas Th2 cells were heavily involved in responses against extracellular pathogens and parasites. Uncontrolled Th1 responses were implicated in autoimmunity and aberrant Th2 responses were associated with allergy and asthma development. However, this model did not explain the observation that a deficiency in Th1 signaling and/or cytokines still allowed the development of autoimmune diseases such as rheumatoid arthritis and multiple sclerosis. More recently (2006) a third subset of CD4 T cells, Th17 cells, which have a pro-inflammatory bias was identified. Subsequent research using animal models and human studies has demonstrated a key role for Th17 cells in the immune system's defense against extracellular bacteria and fungi as well as the development of autoimmune diseases, mediated by the secretion of IL-17 by these cells. The secretion of IL-23 from antigen-presenting cells such as dendritic cells, which have been activated by the uptake and processing of pathogens, in turn activates Th17 cells. (Taken from Bitesized Immunology: https://www.immunology.org/public-information/bitesized-immunology/cells/th17-cells.) See, FIG. 11.

$CD8^+$ (cytotoxic) T cells, like $CD4^+$ Helper T cells, are generated in the thymus and express the T cell receptor. However, rather than the CD4 molecule, cytotoxic T cells express a dimeric coreceptor, CD8, usually composed of one $CD8\alpha$ and one $CD8\beta$ chain. $CD8^+$ T cells recognize peptides presented by MHC Class I molecules, found on all nucleated cells. The CD8 heterodimer binds to a conserved portion (the α3 region) of MHC Class I during T cell/antigen presenting cell interactions (see FIG. 10). CD8+ T cells (often called cytotoxic T lymphocytes, or CTLs) are very important for immune defense against intracellular pathogens, including viruses and bacteria, and for tumor surveillance. When a CD8+ T cell recognizes its antigen and becomes activated, it has three major mechanisms to kill infected or malignant cells. The first is secretion of cytokines, primarily TNF-α and IFN-γ, which have anti-tumor and anti-microbial effects. The second major function is the production and release of cytotoxic granules. These granules, also found in natural killer (NK) cells, contain two families of proteins, perforin, and granzymes. Perforin forms a pore in the membrane of the target cell, similar to the membrane attack complex of complement. This pore allows the granzymes also contained in the cytotoxic granules to enter the infected or malignant cell. Granzymes are serine proteases which cleave the proteins inside the cell, shutting down the production of viral proteins and ultimately resulting in apoptosis of the target cell. The cytotoxic granules are released only in the direction of the target cell, aligned along the immune synapse, to avoid non-specific bystander damage to healthy surrounding tissue (see FIG. 10). CD8+ T cells are able to release their granules, kill an infected cell, then move to a new target and kill again, often referred to as serial killing. The third major function of CD8+ T cell destruction of infected cells is via Fas/FasL interactions. Activated CD8+ T cells express FasL on the cell surface, which binds to its receptor, Fas, on the surface of the target cell. This binding causes the Fas molecules on the surface of the target cell to trimerize, which pulls together signaling molecules. These signaling molecules result in the activation of the caspase cascade, which also results in apoptosis of the target cell. Because CD8+ T cells can express both molecules, Fas/FasL interactions are a mechanism by which CD8+ T cells can kill each other, called fratricide, to eliminate immune effector cells during the contraction phase at the end of an immune response. In addition to their critical role in immune defense against viruses, intracellular bacteria, and tumors, CD8+ T cells can also contribute to an excessive immune response that leads to immunopathology, or immune-mediated damage. (Taken from Bitesized Immunology: https://www.immunology.org/public-information/bitesized-immunology/cells/cd8-t-cells.)

With respect to NK cells, the PK136 monoclonal antibody reacts with mouse NK1.1, an antigen expressed by natural killer cells and a subset of T cells in the NK1.1 mouse strains including C57BL and NZB. Several commonly used laboratory mouse strains such as BALB/c, SJL, AKR, CBA, C3H and A do not express the NK1.1 antigen. For detection of NK cells in these strains the monoclonal antibody DXS 14-5971 is used. Simultaneous staining of C57BL/6 spleen cells with PK136 and DXS reveals coexpression of both markers by a majority of cells as well as presence of small populations of DXS+PK136− and DXS-PK136+ cells.

CD45 (lymphocyte common antigen) and its associated molecules have also been shown to be important for T cell activation. CD45 is a receptor-linked protein tyrosine phosphatase that is expressed on all leucocytes, and which plays a crucial role in the function of these cells. On T cells the extracellular domain of CD45 is expressed in several different isoforms, and the particular isoform(s) expressed depends on the particular subpopulation of cell, their state of maturation, and whether or not they have previously been exposed to antigen. It has been established that the expression of CD45 is essential for the activation of T cells via the TCR, and that different CD45 isoforms display a different ability to support T cell activation. Although the tyrosine phosphatase activity of the intracellular region of CD45 has been shown to be crucial for supporting signal transduction from the TCR, the nature of the ligands for the different isoforms of CD45 have been elusive. Moreover, the precise mechanism by which potential ligands may regulate CD45 function is unclear. Interestingly, in T cells CD45 has been shown to associate with numerous molecules, both membrane associated and intracellular; these include components of the TCR-CD3 complex and CD4/CD8. In addition, CD45 is reported to associate with several intracellular protein tyrosine kinases including R561ck and p59fyn of the src family, and ZAP-70 of the Syk family, and with numerous proteins of 29-34 kDa. These CD45-associated molecules may play an important role in regulating CD45 tyrosine phosphatase activity and function. However, although the role of some of the CD45-associated molecules (e.g. CD45-AP and LPAP) has become better understood in recent years, the role of others still remains obscure. See, Altin and Sloan, (1997) in the reference list herein.

However, these highly promising immunotherapies are only effective for a subset of cancer patients and are not usually curative. In particular, clinical trials of anti-PD-1 antibodies in TNBC patients demonstrate only modest efficacy, with objective responses in the range of 10-20%, and an additional 20% of patients experiencing some stabilization of disease that would otherwise be rapidly progressive (Nanda et al. (2016) [KEYNOTE-012 (ClinicalTrials.gov identifier: NCT01848834) was a multicenter, nonrandomized phase Ib trial of single-agent pembrolizumab given intravenously at 10 mg/kg every 2 weeks to patients with advanced PD-L1-positive (expression in stroma or >1% of tumor cells by immunohistochemistry) TNBC . . . A single-agent phase II study examining a 200-mg dose given once every 3 weeks (ClinicalTrials.gov identifier: NCT02447003) is ongoing.]; Emens et al. (2015) [Pts received MPDL3280A at 15 mg/kg, 20 mg/kg or 1200 mg flat dose IV q3w]; Dirix et al. (2015) [Pts received avelumab at 10 mg/kg Q2W until confirmed progression, unacceptable toxicity, or any criterion for withdrawal occurred.]; Rugo et al. (2015) [Pembrolizumab was administered at a dose of 10 mg/kg every 2 weeks for up to 24 months or until confirmed progression or intolerable toxicity.]; Dawood and Rugo (2016)). There is thus a pressing clinical need to identify better therapies to improve individual responses to immunotherapy.

PD-1 and its ligand PD-L1 are immune checkpoint molecules that dampen T cell immunity (Lin et al. (2010); Curiel et al. (2003); Brahmer et al. (2012); Pardoll and Drake (2012); Pardoll (2012)). PD-L1 is overexpressed in tumor cells and some immune cells, including Tregs (Lin et al. (2010); Curiel et al. (2003); Pardoll (2012); Topalian et al. 2012)). Immunotherapy with anti-PD-1 ((αPD-1) and anti-PD-L1 antibodies (αPD-L1) has proven successful for treating various cancers (Brahmer (2012); Pardoll and Drake (2012); Pardoll (2012)). Early clinical trials for TNBC indicate that PD-1 and PD-L1 are valid targets for intervention and toxicities of treatment are mild. In a Phase 1 study of 27 women with heavily pretreated, chemotherapy resistant, metastatic TNBC that expressed PD-L1, the response rate was 18.4% to pembrolizumab, an αPD-1 antibody (Nanda et al. 2016). A similar study of atezolizumab, an αPD-L1 antibody, produced a response rate of 19% in 21 evaluable, PD-L1 expressing TNBC tumors (Emens et al. (2015); Dawood and Rugo (2016)). Another group reported an 8.6% response rate to avelumab, another αPD-L1 antibody, in 168 TNBC tumors unselected for PD-L1 expression (Dirix et al. 2015), indicating that level of PD-L 1 tumor expression may be important in mediating tumor response. Some disease stabilization was seen in this aggressive subtype of breast cancer, in approximately 20% of patients in these 3 trials. Serious toxicities were few and related to immune modulation. These clinical data indicate that the PD-1/PD-L1 axis can be a therapeutic target specifically in TNBC, likely in combination approaches for better efficacy.

There are two distinct types of estrogen receptors that mediate diverse physiological effects of estrogens on breast cancer cells. The first receptor is the ERα receptor which supports estrogen-dependent breast tumor growth. The second is the ERβ receptor which appears to work in an opposite fashion to significantly attenuate the growth of breast tumor cells in preclinical models (Clarke et al. (2003); Deroo and Korach (2006); Deroo and Buensuceso (2010); Honma et al (2008); Katzenellenbogen and Katzenellenbogen (2000); McDonnell and Norris (2002); Murphy and Watson (2006); Shaaban et al (2008). Thus, ERβ can be viewed in as a tumor suppressor gene in breast cancer. ERβ is expressed in about 40% of TNBC cancers, and the therapeutic potentials of targeting ERβ have not yet been investigated in TNBC. Two recent advances have now made it feasible to move from the preclinical models and into clinical research. The first advance is a newly discovered mechanism of rallying ERβ's antitumor activity (Harris (2007); Hartman et al (2009); Heldring et al. (2007); Thomas and Gustafsson (2011)), and the second is the development of an oral formulation of an ERβ agonist (S-equol) that has already been tested for clinical safety, pharmacodynamics and tolerance in humans (Jackson et al. (2011a & b); Setchell et al. (20005); Setchell (2002); Schwen et al. (2012).

Estrogen receptor (ERβ; nuclear or cytoplasmic) is reported to be present in approximately half of TNBC (Marotti et al. (2010); Reese et al. (2014)). Thus, rallying ERβ antitumor activity through ERβ-specific modification and/or ligand binding represents an excellent therapeutic opportunity for TNBC. However, the therapeutic potentials of targeting ERβ have not been extensively exploited, partly due to the paucity in the knowledge of how to harness its antitumor activity. A phosphotyrosine residue (Y36) in ERβ, but not ERα, has recently been identified that is important for regulating the antitumor activity of ERβ in TNBC cells (Yuan et al. (2014); Yuan et al. (2016)).

When this phosphotyrosine residue (pY36) was purposefully mutated by adding a phenylalanine group (Y36F), activation of ERβ target genes were decreased in a TNBC cell line (MDA-MB-231). The Y36F mutation also obliterated the ability of ERβ to inhibit tumor cell growth in vitro and in vivo. This preclinical research therefore strongly supports the importance of pY36 in the antitumor activity of ERβ (Yuan et al., 2014).

There is also evidence that pY36 status correlates with survival of breast cancer patients. Research has been done using a Prognostic Tissue Microarray (TMA) from the National Cancer Institute (NCI), which consists of a large cohort of breast tumor samples with a clinical follow-up record. Using a total of 726 readable IHC samples, patients with pY36-negative tumors were found to have statistically significant shorter disease-free and overall survival than those with pY36-positive tumors. Interestingly, the association with survival was only seen in Stage II & III disease, which raises the intriguing possibility that pY36 activity may have an effect on disease progression from locally advanced to metastatic breast cancer. Collectively, pY36 intensity appears to have a stronger correlation with patient outcome than total ERβ, underscoring the clinical importance of this previously unappreciated phosphotyrosine switch. See, FIG. 14.

S-equol, an ERβ agonist, was previously shown to increase respiratory and maximal glycolysis fluxes in rat hippocampal neurons, as well as cytochrome oxidase (COX) activity and COX1 protein levels in brains from ovariectomized mice, and has been studied in human subjects to assess its health impact and safety (Yao et al. (2013); Jenks et al. (2002); Jackson et al. (2011a & b); Usui et al., (2013)).

S-equol can be produced either chemically (i.e., chemical synthesis) or by biotransformation (biosynthesis) through the metabolism of daidzein, an isoflavone found in soy and red clover, by gut bacteria. The structure of S-equol is shown below.

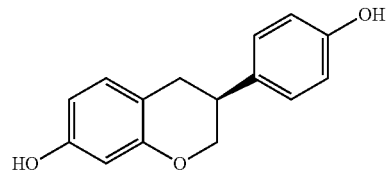 [SMILES: Oc1ccc([C@H]2COc3cc(O)ccc3C2)cc1]

Equol has a chiral center and therefore can exist in two enantiomeric forms. S-equol, R-equol, racemic equol, and non-racemic mixtures of equol (collectively "equol"); compositions of equol; anhydrous crystalline polymorph of equol; processes for the preparation of equol; and methods of using equol are described in U.S. Pat. No. 8,716,497 (filed Sep. 10, 2012); U.S. Pat. No. 8,048,913 (filed Sep. 14, 2009); U.S. Pat. No. 7,960,432 (filed Jul. 3, 2008); U.S. Pat. No. 7,396,855 (filed Jul. 24, 2003); U.S. Pat. No. 8,263,790 (filed Jun. 1, 2011); U.S. Pat. No. 7,960,573 (filed May 4, 2009); U.S. Pat. No. 7,528,267 (filed Aug. 1, 2005); U.S. Pat. No. 8,668,914 (filed Jul. 31, 2009); U.S. Pat. No. 8,580,846 (filed Aug. 18, 2006); U.S. Pat. No. 8,450,364 (filed Apr. 9, 2012); and U.S. Pat. No. 8,153,684 (filed Oct. 2, 2009); U.S. Pat. No. 9,408,824 (filed Mar. 5, 2014); and U.S. Pat. No. 9,914,718 (filed Oct. 14, 2015); each of which is hereby incorporated by reference in its entirety.

Formulations comprising isoflavones and products derived therefrom have been used in the past to treat disease. For example, a mixture of equol, genistein, and daidzein, or a mixture of equol, genistein, daidzein, and IBSO03569 have shown potential for treating or preventing neurodegeneration and Alzheimer's disease. See Zhao et al. (2009); U.S. Pat. No. 8,552,057; Yao et al. (2013) (collectively "Brinton et al."). S-equol alone has also been described for treating Alzheimer's Disease. See, U.S. application Ser. No. 15/659, 114 published as U.S. Patent Publication 2018/0028491, and International Patent Publication WO/2018/022604, which are hereby incorporated by reference in their entireties.

However, there remains a need in the art for methods that utilize S-equol for the treatment of other disease states that have in the past been difficult to treat. In particular, there is a need in the art for methods that utilize S-equol in the treatment of breast cancer, and even more particularly where the breast cancer tumors are negative for estrogen receptor α, progesterone receptor and HER-2 receptor ("triple-negative breast cancer"), and thus not treatable with known agonists and antagonists of those receptors.

SUMMARY OF THE INVENTION

The following brief summary is not intended to include all features and aspects of the present invention, nor does it imply that the invention must include all features and aspects discussed in this summary.

The inventors have found that S-equol, preferably pure and isolated S-equol, can benefit breast cancer patients. In particular, the inventors have found that S-equol in combination with immunotherapy is particularly effective in treating breast cancer, and in particular, triple-negative breast cancer.

It is therefore an object of the invention to provide the following:

1. A method for treating or preventing breast cancer, by administering a pharmaceutically effective amount of a formulation comprising S-equol to a subject in need thereof.
2. The method of Item 1, wherein the subject has been diagnosed with triple-negative breast cancer.
3. The method of Item 1, wherein the formulation comprises 10-200 mg S-equol.
4. The method of Item 1, wherein the formulation comprises 50-150 mg S-equol.
5. The method of Item 1, wherein the formulation comprises about 50 mg S-equol.
6. The method of Item 1, wherein the formulation comprises about 150 mg S-equol.
7. The method of Item 1, wherein the formulation is administered orally, intravenously, intraperitoneally, or subcutaneously.
8. The method of Item 1, wherein said subject is a human.
9. The method of Item 1, wherein the S-equol is administered in combination with one or more other cancer treatments.
10. The method of Item 9, wherein the S-equol is administered in combination with an immunotherapeutic agent.
11. The method of Item 10, wherein the immunotherapeutic agent is an antibody.
12. The method of Item 11, wherein the antibody is directed to programmed cell death protein 1 (PD-1).
13. The method of Item 12, wherein the antibody is directed to programmed death ligand 1 (PDL-1).
14. The method of Item 12, wherein the antibody is pembrolizumab.
15. The method of Item 13, wherein the antibody is atezolizumab.
16. The method of Item 13, wherein the antibody is avelumab.
17. The method of Item 1, wherein the formulation is essentially free of genistein, daidzein, and/or IBSO03569.
18. The method of Item 1, wherein genistein, daidzein, and/or IBSO03569 are not co-administered with S-equol.
19. The method of Item 1, wherein the formulation is essentially free of R-equol.
20. The method of Item 1, wherein the S-equol is produced chemically.
21. The method of Item 1, wherein the formulation is administered once per day.
22. The method of Item 1, wherein the formulation is administered twice per day.
23. The method of Item 1, wherein the formulation is administered three times per day.
24. The method of Item 1, wherein the formulation is administered four times per day.

The invention also relates to compositions comprising S-equol as described for the methods herein. The invention also includes articles of commerce comprising a composition that comprises a non-racemic mixture of equol, and typically comprises equol consisting essentially of S-equol.

The foregoing and other objects, features and advantages of the invention will be apparent from the following more particular description of preferred embodiments of the invention, as illustrated in the accompanying drawings in which like reference characters refer to the same parts throughout the different views.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1A shows an immunoblot of mouse ERβ in tissues from WT, KO, and KI animals. Ponceau S staining for protein loading. FIG. 1B shows WT and KI female mice (n=8) were orthotopically injected with syngeneic murine mammary tumor cells (M-Wnt1, $1\times10^4$). *p<0.05.

FIG. 2A shows the schema for the chimera experiments. FIG. 2B shows tumor growth in chimeric mice (WT>WT: n=10, KI>WT: n=4). p=0.0003. FIG. 2C shows total $CD8^+$ T cells from tumors. FIG. 2D shows interferon gamma (IFN-γ) expressing $CD8^+$ T cells from tumors.

FIG. 4A shows that separately, S-equol and anti-PD-1 antibody reduce tumor volume compared to control, but S-equol in combination with an anti-PD-1 antibody reduces tumor volume compared to S-equol or anti-PD-1 antibody alone over 35 days post-challenge. FIG. 4B shows that separately, S-equol and anti-PD-1 antibody reduce tumor weight compared to control, but S-equol in combination with an anti-PD-1 antibody reduces tumor weight compared to S-equol or anti-PD-1 antibody alone. FIG. 4C shows tumors from mice treated with vehicle+IgG2a, S-equol+IgG2a, vehicle+anti-PD-1 antibody and S-equol+anti-PD-1 antibody and that separately, S-equol and anti-PD-1 antibody reduce tumor size compared to control, but S-equol in combination with an anti-PD-1 antibody reduces tumor size compared to S-equol or anti-PD-1 antibody alone.

FIG. 5A shows that the percentage of $CD45^+CD3^+$ cells increased in mice treated with S-equol plus an anti-PD-1 antibody compared to mice treated with S-equol or anti-PD-1 antibody alone. FIG. 5B shows $CD4^+$ cells decreased in mice treated with S-equol plus an anti-PD-1 antibody compared to mice treated with S-equol or anti-PD-1 antibody alone. FIG. 5C shows $CD8^+$ cells increased in mice treated with S-equol plus an anti-PD-1 antibody compared to mice treated with S-equol or anti-PD-1 antibody alone. FIG. 5D shows $NK1.1^+$ cells increased in mice treated with S-equol plus an anti-PD-1 antibody compared to mice treated with S-equol or anti-PD-1 antibody alone.

FIG. 6 shows that S-equol plus an anti-PD-1 antibody reduces tumor volume compared to S-equol or anti-PD-1 antibody alone over 28 days post-challenge.

FIG. 7A shows tumors from mice treated with vehicle+IgG2a, S-equol+IgG2a, vehicle+anti-PD-1 antibody and S-equol+anti-PD-1 antibody. FIG. 7B shows that S-equol plus an anti-PD-1 antibody reduces tumor weight compared to S-equol or anti-PD-1 antibody alone.

FIG. 14A shows the Kaplan-Meier estimate of disease-free and overall survival in Stages II-III specimens correlating with IHC intensity of pY36-ERβ. FIG. 14B shows the Kaplan-Meier estimate of disease-free and overall survival in Stages II-III specimens correlating with IHC intensity of (A) and total ERβ IHC.

FIG. 15A shows Ki-67 positivity in tumors of control and S-equol treated mice. FIG. 15B shows images of Ki-67 immunohistochemistry (TIC; ×40).

FIG. 16A shows tumor volume over 28 days post-tumor challenge with either vehicle plus α-IgG2a (blue line), S-equol plus α-IgG2a (red line), vehicle plus α-PD-1 (purple line) and S-equol plus α-PD-1 (green line). FIG. 16B shows EMT6 tumor weight post-tumor challenge with either vehicle plus α-IgG2a (blue dots), S-equol plus α-IgG2a (red dots), vehicle plus α-PD-1 (purple dots) and S-equol plus α-PD-1 (greendots). FIG. 16C shows the size of tumors post-tumor challenge with either vehicle plus α-IgG2a (top row), S-equol plus α-IgG2a (second row from top), vehicle plus α-PD-1 (third row from top) and S-equol plus α-PD-1 (bottom row).

FIG. 17A shows CD45 expression. FIG. 17A shows CD45 expression. FIG. 17B shows CD8 expression. FIG. 17C shows CD4 expression. FIG. 17D shows NK1.1 expression. FIG. 17E shows CD107a expression as percent CD3 expression. FIG. 17F shows CD107a expression as percent CD8 expression. FIG. 17G shows CD107a expression as percent CD4 expression. FIG. 17H shows CD107a expression as percent NK1.1 expression.

FIG. 18A shows that a pY36-specific phosphorylation signal was enhanced by the ERd/ERβ common agonist 17-β-estradiol and two ERβ-specific agonists diarylpropionitrile (DPN) and S-equol in MDA-MB-231 cells. FIG. 18B shows that S-equol treatment inhibited MDA-MB-231 cell-derived xenograft tumor growth (n=5). FIG. 18C shows expression of Ki67 in xenograft tumors. FIG. 18D shows ERβ-pY36 signal in vehicle- and S-equol-treated xenograft tumor samples. *p.0.05, **p<0.01. See, Yuan et al. (2016) listed below, which is incorporated by reference herein for all purposes.

DETAILED DESCRIPTION OF THE INVENTION

Figure 1A:
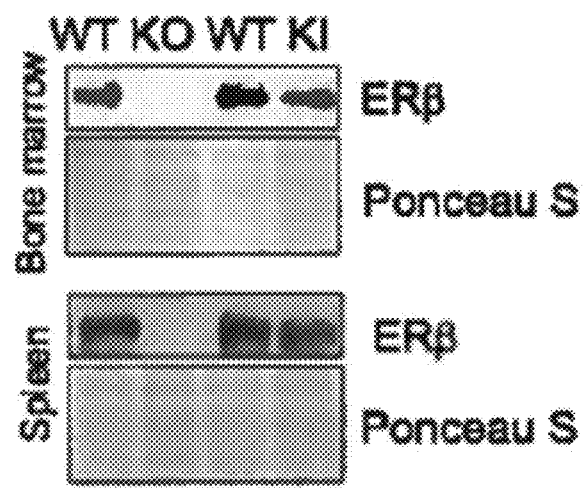
FIGS. 1A-1B. Host effect of ERβ signaling on tumor growth.

Unless defined otherwise, all technical and scientific terms used herein have the same meaning as commonly understood by those of ordinary skill in the art to which this invention belongs. Although any methods and materials similar or equivalent to those described herein can be used in the practice or testing of the present invention, the preferred methods and materials are described. Generally, nomenclatures utilized in connection with, and techniques of, cell and molecular biology and chemistry are those well-known and commonly used in the art. Certain experimental techniques, not specifically defined, are generally performed according to conventional methods well known in the art and as described in various general and more specific references that are cited and discussed throughout the present specification. For purposes of clarity, the following terms are defined below.

"Substantially pure" means about 90% pure, preferably 95% pure, and more preferably 98% pure of any contaminating proteins.

"Substantially free" means about less than about 10%, preferably less than 5%, and more preferably less than 2% of any contaminating proteins.

"Approximately" or "about" means within +/−10%, preferably within +/−5%, more preferably within +/−2% of that which is being measured.

"TNBC tumors" are defined as less than or equal to 5% nuclear staining of carcinoma cells for ER-alpha and PR and either 0, 1+ or 2+ staining for HER-2 by IHC. If only fluorescence in situ hybridization (FISH) is performed for HER-2, it must be less than or equal to 2.0. Tumor cells that show distinct nuclear staining of total ER-beta or pY36 (regardless of cytoplasmic staining) will be scored as positive.

The present invention relates to the prevention and/or treatment of breast cancer with S-equol. The inventors have found that S-equol is a particularly useful treatment for triple-negative breast cancer (TNBC), for which effective immunotherapies are limited.

Dosage amounts and administration schedules for S-equol will depend on whether the S-equol is being administered prophylactically to a patient at risk of developing breast cancer, or being administered as treatment for a patient already diagnosed with breast cancer. A person at risk for developing breast cancer may be a person with a family history of breast cancer, and/or may have one or more mutations in a BRCA1 or BRCA2 gene. In a patient already diagnosed with breast cancer, dosages and administration schedules may also vary depending on the stage of the cancer (stage I, stage II, stage III, stage IV or stage V), the number of lymph nodes involved, tumor size and the availability of and/or decision to co-administer other therapies. Dosages and administration schedules may also vary depending on various molecular markers present on or in tumor cells, including, but not limited to ERα, PR, HER2, Ki67 and pY36. Diagnostic tests for markers which are prognostic for the aggressiveness and/or likelihood of recurrence of a tumor include the OncotypeDX® Breast Cancer Test, MammaPrint®, PAM-50 ROR®, EndoPredict® and the Breast Cancer Index®. Such markers include, but are not limited to proliferation genes such as Ki67, STK15, Survivin, CCNB1 (Cycline B1), MYBL2, invasion genes such as MMP11 (Stromolysin 3), CTSL2 (Cathepsin L2), HER2 genes GRB2 and HER2, Estrogen genes ER, PGR, BCL2 and SCUBE2 and other cancer related genes such as GSTM1, CD68 and BAG1. (Kittaneh et al. (2013); see also, Coates et al. (2015), both of which are hereby incorporated by reference in their entireties for all purposes.)

S-equol can be administered one or more times per day at 1-400 mg per dose, more preferably 10-320 mg, more preferably 50-150 mg. Non-limiting examples include 2 mg, 5 mg, 10 mg, 15 mg, 20 mg, 40 mg, 50 mg, 80 mg, 100 mg, 150 mg, 160 mg, 200 mg, 250 mg, 300 mg 320 mg, etc. or approximately or about those doses. The dose may be administered one, two, three or four times per day, preferably twice per day (B.I.D.) The regimen can be continued indefinitely, or for such time in intervals where markers are examined and responsiveness to the dose is determined. Examples of such intervals are two weeks, four weeks, two months, four months, six months, etc. or about or approximately those intervals. No upper limit, with respect to administration schedule, is required.

The S-equol administered is preferably formulated for oral administration; however, other routes of administration are also contemplated, including rectal, optical, buccal (for example sublingual), parenteral (for example subcutaneous, intramuscular, intradermal and intravenous) and transdermal administration.

Compositions or formulations according to the present invention can comprise one or more pharmaceutically-acceptable or industrial standard fillers. The filler must not be deleterious to a subject treated with the composition. The filler can be solid or a liquid, or both. The filler can be formulated with the active S-equol as a unit-dose, for example a tablet, which can typically contain from about 10% to 80% by weight of S-equol. Compositions can be prepared by any of the well known techniques of pharmacy, for example admixing the components, optionally including excipients, diluents (for example water) and auxiliaries as are well known in the pharmaceutical field.

Compositions suitable for oral administration can be presented in discrete units, such as capsules, cachets, lozenges, or tablets, each containing a predetermined amount of the extract; as a powder or granules; as a solution or a suspension in an aqueous or non-aqueous liquid; or as an oil-in-water or water-in-oil emulsion. Such compositions can be prepared by any suitable method of pharmacy which includes the step of bringing into association the active S-equol and one or more suitable carriers (which can contain one or more accessory ingredients as noted above). In general the compositions of the invention are prepared by uniformly and intimately admixing the S-equol with a liquid or finely divided solid carrier, or both, and then, if necessary, shaping the resulting mixture. For example, a tablet can be prepared by comprising or moulding a powder or granules containing the extract, optionally with one or more accessory ingredients. Compressed tablets can be prepared by compressing in a suitable machine, the extracts in the form of a powder or granules optionally mixed with a binder, lubricant, inert diluents, and/or surface active/dispersing agent(s). Moulded tablets can be made by moulding, in a suitable machine, the powdered compound moistened with an inert liquid binder.

Suitable fillers, such as sugars, for example lactose, saccharose, mannitol or sorbitol, cellulose preparations and/or calcium phosphates, for example tricalcium phosphate or calcium hydrogen phosphate, and also binders such as starch pastes using, for example, corn, wheat, rice or potato starch, gelatin, tragacanth, methylceullose and/or polyvinylpyrrolidone, and, if desired, disintegrators, such as the abovementioned starches, also carboxymethyl starch, cross linked polyvinyl pyrrolidone, agar or alginic acid or a salt thereof, such as sodium alginate. Excipients can be flow conditioners and lubricants, for example silicic acid, talc, stearic acid or salts thereof, such as magnesium or calcium stearate, and/or polyethylene glycol. Dragee cores are provided with suitable, optionally enteric, coatings, there being used, inter alia, concentrated sugar solutions which can comprise gum arabic, talc, polyvinylpyrrolidone, polyethylene glycol and/or titanium dioxide, or coating solutions in suitable organic solvents or solvent mixtures, or, for the preparation of enteric coatings, solutions of suitable cellulose preparations, such as microcrystalline cellulose, acetylcellulose phthalate or hydroxypropylmethylcellulose phthalate. Dyes or pigments can be added to the tablets or dragee coatings, for example for identification purposes or to indicate different doses of active ingredients.

Other orally administrable pharmaceutical compositions are dry-filled capsules made, for example, of gelatin, and soft, sealed capsules made of gelatin and a plasticiser, such as glycerol or sorbitol. The dry-filled capsules can comprise the extracts in the form of granules, for example in admixture with fillers, such as lactose, binders, such as starches, and/or glicants, such as talc or magnesium stearate, and, where appropriate, stabilizers. In soft capsules, the extract is preferably dissolved or suspended in suitable liquids, such as fatty oils, paraffin oil or liquid polyethylene glycols, to which stabilizers can also be added.

According to one aspect of the invention, the compositions comprising S-equol include those described in U.S. Pat. No. 7,960,432 (filed Jul. 3, 2008); U.S. Pat. No. 7,396,855 (filed Jul. 24, 2003); and U.S. Pat. No. 9,408,824 (filed Mar. 5, 2014)—the disclosures of each are hereby incorporated by reference in their entireties.

According to another aspect of the invention, S-equol can be prepared chemically (i.e., chemical synthesis) according to the processes described in U.S. Pat. No. 8,716,497 (filed Sep. 10, 2012); U.S. Pat. No. 8,263,790 (filed Jun. 1, 2011); U.S. Pat. No. 7,960,573 (filed May 4, 2009); U.S. Pat. No. 7,528,267 (filed Aug. 1, 2005) and U.S. Pat. No. 9,914,718 (filed Oct. 14, 2014)—the disclosures of each are hereby incorporated by reference in their entireties. For example, S-equol can be enantioselectively prepared using an iridium catalyst with a chiral ligand. These methods of enantioselectively preparing S-equol are incorporated by reference.

According to another aspect of the invention, S-equol can be a single anhydrous crystalline polymorph of S-equol, such as the anhydrous crystalline polymorph of S-equol described in U.S. Pat. No. 9,914,718 (application Ser. No. 14/883,617, filed Oct. 14, 2015)—the disclosure of which, including the chemical and physical properties used to characterize the anhydrous crystalline polymorph of S-equol, is incorporated by reference in their entireties. For example, the anhydrous crystalline polymorph of S-equol described in U.S. Patent Application Publication No. 2016/0102070 has the following characteristic X-ray powder diffraction pattern wavenumbers ($cm^1$): 3433, 3023, 3003, 2908, 2844, 1889, 1614, 1594, 1517, 1508, 1469, 1454, 1438, 1400, 1361, 1323, 1295, 1276, 1261, 1234, 1213, 1176, 1156, 1116, 1064, 1020, 935, 897, 865, 840, 825, 810, 769, 734, 631, 616, 547, 517, 480, and 461. The characterizations of anhydrous crystalline polymorph of S-equol are incorporated by reference.

S-equol can be administered in combination with one or more additional cancer treatments, including surgery (breast+/−axilla), cytotoxic chemotherapy, radiation, immunotherapy, cancer vaccines, inhibitors of cellular pathways (protein or peptide, nucleic acid-based [antisense oligonucleotides including DNA oligonucleotides, antisense siRNA, shRNA] and/or hormonal (adjuvant endocrine) therapy. Examples of cytotoxic chemotherapy suitable for treating breast cancer include, but are not limited to anthracyclines such as doxorubicin (Adriamycin®) and epirubicin (Ellence®), taxanes such as paclitaxel (Taxol®) and docetaxel (Taxotere®), 5-fluorouracil (5-FU), capecitabine, cyclophosphamide (Cytoxan®) and carboplatin (Paraplatin®). Examples of adjuvant endocrine therapy include tamoxifen and aromatase inhibitors such as anastrozole (Arimedix®), exemestane (Aromasin®) and Letrozole (Femara®). Examples of immunotherapy include but are not limited to pembrolizumab (Keytruda®, MK-3475), nivolumab (Opdivo®), durvalumab (MEDI4736), tremelimumab, atezolizumab (MPDL3280A), avelumab, trastuzumab, PDR001, and MGD009. An example of a known inhibitor of a cellular pathway is a tyrosine kinase inhibitor such as lapatinib. Appropriate dosages of immunotherapy monoclonal antibodies or other cancer therapeutic are determined based on the indication, and their determination is well within the skill in the art. Dosing may be in mg, in mg/kg or mg/m$^2$. See, Sachs et al. (2016), which is incorporated by reference herein in its entirety for all purposes, including examples of therapeutic antibodies, small molecules and dosages. Pembrolizumab (marketed as Keytruda by Merck) was the first mAb approved in the United States targeting PDCD1 (PD-1) receptor. The dosing strategy for this novel immuno-oncology compound was driven by understanding of BED. First, an optimally designed, 13-patient, within-subject dose escalation study focused on elucidating the pharmacokinetic-pharmacodynamic relationship by measuring IL2 response over a 2,000-fold dose range of 0.005 to 10 mg/kg (25). The BED was estimated to be 2 mg/kg because IL2 stimulation approached saturation at exposures consistent with this dose. The BED of 2 mg/kg and maximum administered dose of 10 mg/kg were explored in later clinical studies. Early clinical response measured by change in tumor size from baseline was used to perform exposure-response analysis demonstrating similar antitumor response over the dose range from 2 to 10 mg/kg (26). The S-equol and/or additional therapeutic composition may be administered once, twice, three times or more per day, depending on the dose, toxicity and indication. Dosing may occur over several days, weeks or months, and may be continuous or intermittent. Typical dosages for immunotherapeutics are 50-500 mg/day, more preferably 100-400 mg/day, more preferably 150-250 mg/day. In certain embodiments, the dose may be 150 mg/day or 150 mg twice per day, or 250 mg/day or 250 mg twice a day. In other embodiments the dosage may be given based on patient weight, for instance 0.5-10 mg/kg, more preferably about 1, 2 or 5 mg/kg. Dosage may also be given as mg/m$^2$, for example 50-500 mg/m$^2$, more preferably 100-300 mg/m$^2$, for example about 100, 150, 200, 250 or 300 mg/m$^2$.

The dosages may be about or greater than the lower end of any of the afore-stated ranges, or about or less than the upper end of any of the afore-stated ranges.

Responsiveness to the S-equol+/−other cancer therapy can be assessed by analyzing one or more cellular markers, by imaging techniques, by cellular proliferation assays and by direct examination of tumors. The analysis of cellular markers can be done with immunohistochemical or immunocytochemical techniques or by nucleic acid detection, such as hybridization techniques and polymerase chain reaction (PCR). A preferred biomarker to assess mitotic division and tumor growth is Ki67 (Beelen et al. (2012); Urruticoechea et al. (2005)).

The following examples are provided to aid the understanding of the present invention, the true scope of which is set forth in the appended claims. It is understood that modifications can be made in the procedures set forth without departing from the spirit of the invention.

EXAMPLES

The processes of the present invention will be better understood in connection with the following examples, which are intended as an illustration only and without limiting the scope of the invention. Various changes and modifications to the disclosed embodiments will be apparent to those skilled in the art and such changes and modifications including, without limitation, those relating to the processes, formulations and/or methods of the invention may be made without departing from the spirit of the invention and the scope of the appended claims.

Example 1

Figure 1B:
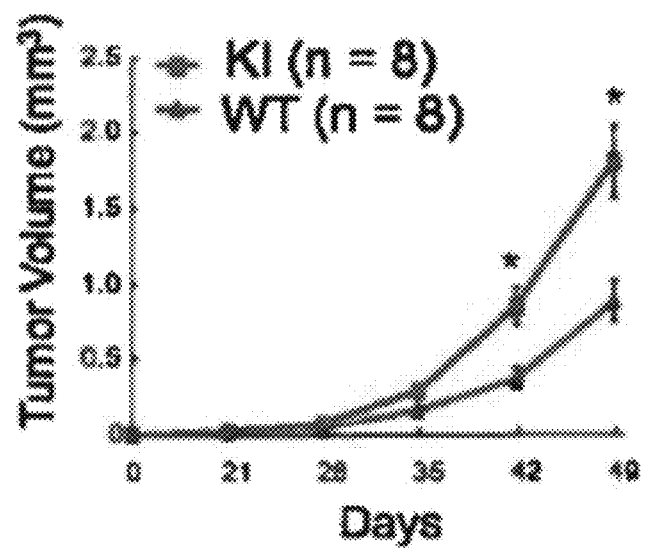

To determine whether the newly identified phosphotyrosine switch regulates ERβ tumor-extrinsic function, a whole-body knock-in (KI) mouse model (C57BL/6) was established in which the corresponding tyrosine residue of endogenous mouse ERβ is mutated to phenylalanine (Y-F). Consistent with previously reported ERβ knockout (KO) mice (Krege et al. (1998)), these phosphorylation mutant KI mice had no overt developmental defects and were grossly indistinguishable from their WT littermates (unpublished data). Survey of ERβ expression in KO and KI mice indicated that the Y-F mutant protein was expressed at levels comparable to WT ERβ in multiple tissues, including bone marrow and spleen (FIG. 1A). Syngeneic murine tumor cells of various origins were then transplanted, including the MMTV-Wnt mammary tumor cell line with a basal-like breast cancer profile (Pfefferle et al. (2013)), into WT and KI recipient mice. In all cases, tumor cells grew more robustly in ERβ KI recipient mice than in their syngeneic WT counterparts (FIG. 1B, and data not shown). These data clearly demonstrate that the phosphotyrosine switch is important for ERβ tumor-extrinsic antitumor activity in multiple tumor types.

Example 2

Figure 2A:
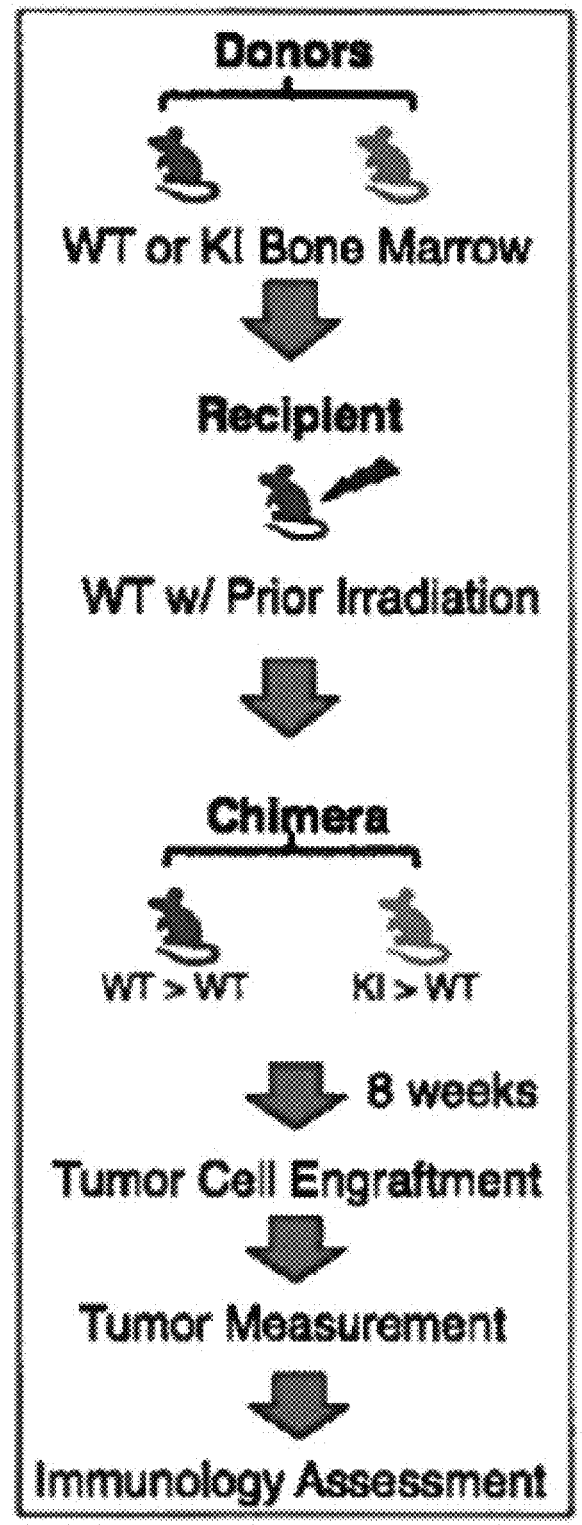
FIGS. 2A-2D. A role of ERβ signaling in immune cells.
Figure 2B:
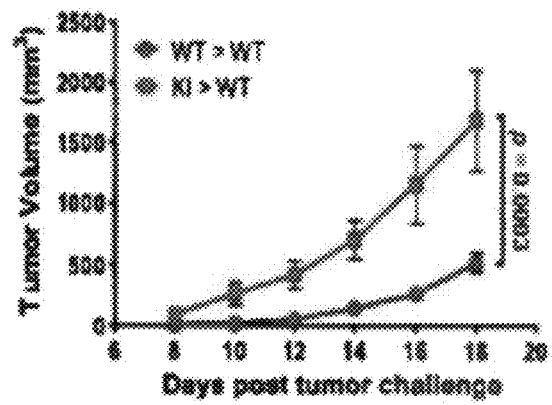

The following experiment sought to delineate further the host ERβ signaling in tumor inhibition based on the role of antitumor immunity and recent clinical advances in cancer immunotherapies (Topalian et al. (2015); Chen and Flies (2013); Sharma and Allison (2015)). A mouse chimera experiment was conducted involving a bone marrow transplant. As illustrated in FIG. 2A, WT recipient mice were first irradiated (10 Gy) to kill endogenous bone marrow cells, followed by transplant with bone marrow from syngeneic KI or WT donors. After confirming successful chimerism in KI>WT and WT>WT mice, tumor cells were injected 8 weeks after bone marrow transplant. Tumor growth was significantly greater in KI>WT chimeras (with KI immune cells) versus WT>WT controls (FIG. 2B). This suggests that KI immune cells poorly controlled tumor growth. Thus, these data link the importance of tumor extrinsic ERβ antitumor activity to the immune response.

Example 3

Figure 2C:
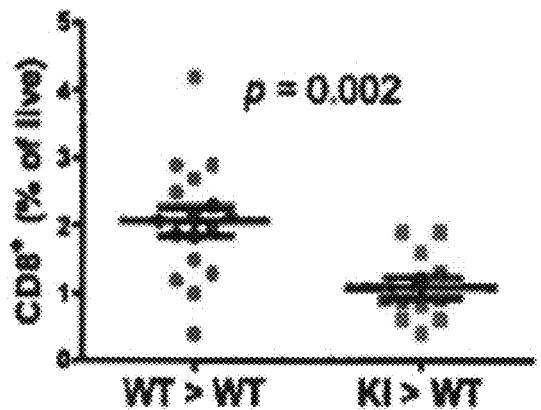
Figure 2D:
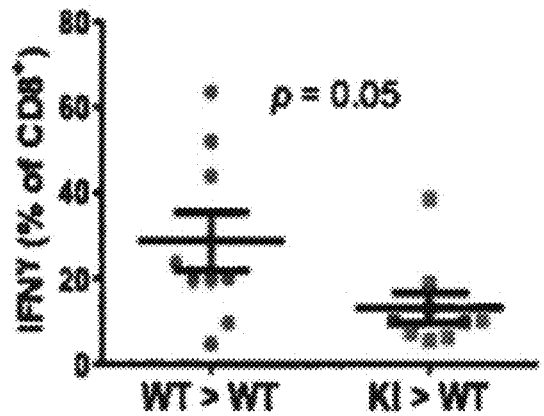

Next, tumor-infiltrating immune cell populations were analyzed. Total numbers of tumor-infiltrating CD4$^+$ and CD8$^+$ T cells were reduced in KI>WT versus WT>WT mice (FIG. 2C and data not shown), further supporting the notion that antitumor immunity in KI mice is compromised. Furthermore, the prevalence of IFNγ-producing CD8$^+$ (antitumor) cells was significantly lower in tumors from KI>WT versus WT>WT mice (FIG. 2D), suggesting compromised cytotoxic potency of CD8$^+$ T cells in the absence of functional ERβ signaling. Additional preliminary data not shown here indicate that activation of dendritic cells, which prime antitumor T cells, was also compromised in KI>WT chimeric mice, as evidenced by their reduced MHC-II expression. Furthermore, effector T cells were less activated (lower CD44/CD62L) and had other reduced effector functions in KI>WT chimeras [e.g., lower tumor necrosis factor alpha (TNF)α, interleukin (IL)-2, and perforin, data not shown]. These data strongly suggest ERβ-dependent augmentation of antitumor CD8$^+$ T cell effector activity and improved intra-tumor immune cell accumulation. Therefore, rallying ERβ antitumor activity with clinically safe ERβ agonists such as S-equol will improve efficacy of existing anticancer immunotherapies and make them more effective to treat TNBC.

Example 4

Figure 3:
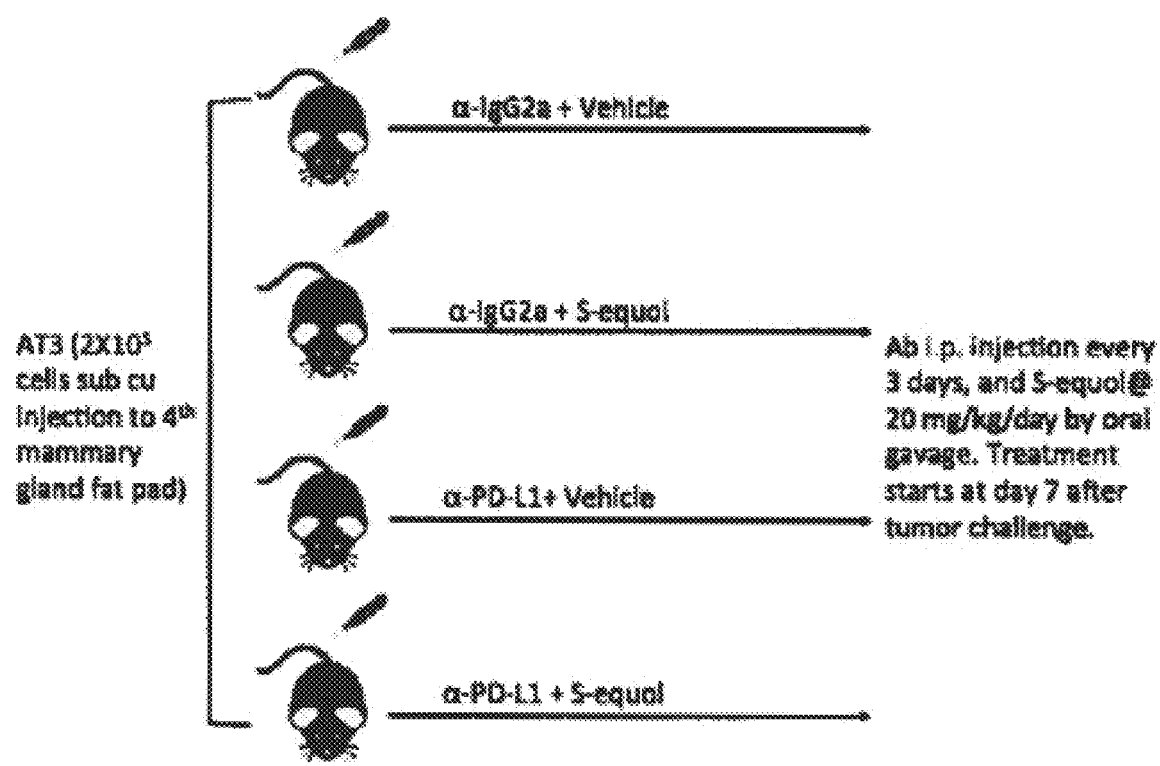
FIG. 3. A schema for combination therapy.
Figure 4A:
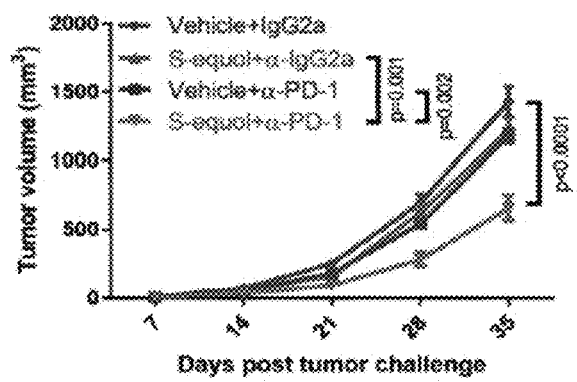
FIGS. 4A-4C. Effect of S-equol in combination with an anti-PD-1 antibody on mice challenged with an AT3 mammary tumor cell line. Mice were administered anti-PD-1 antibody at 200 μg every 3 days and S-equol at 50 mg/kg per day.
Figure 4B:
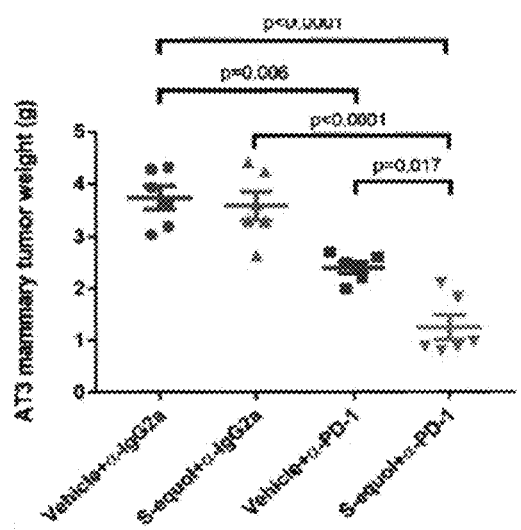
Figure 4C:
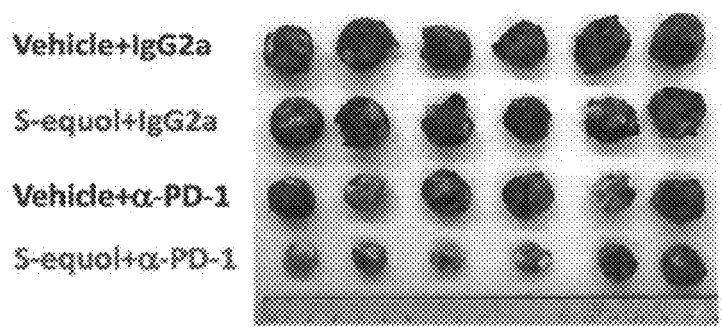
Figure 5A:
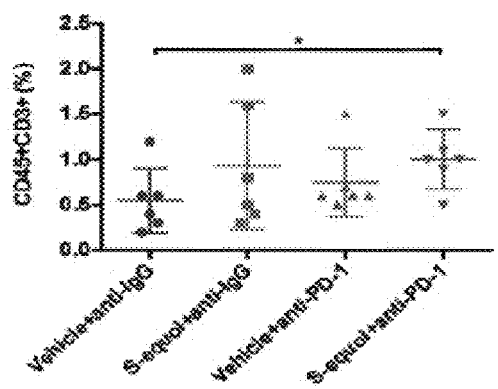
FIGS. 5A-5D. Analysis of tumor-infiltrating lymphocytes.
Figure 5B:
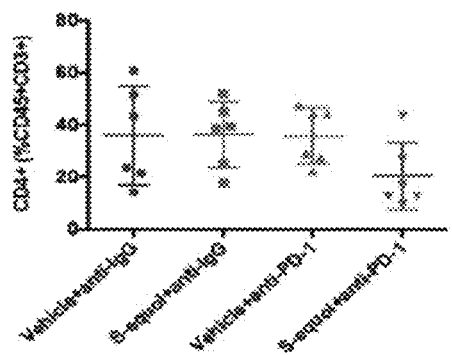
Figure 5C:
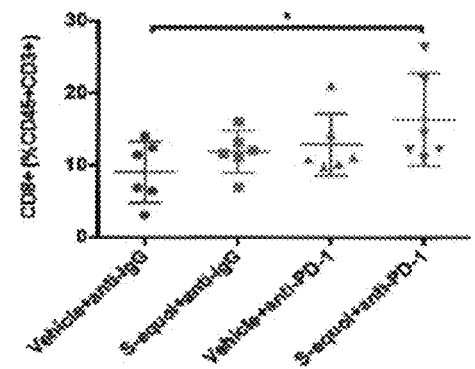
Figure 5D:
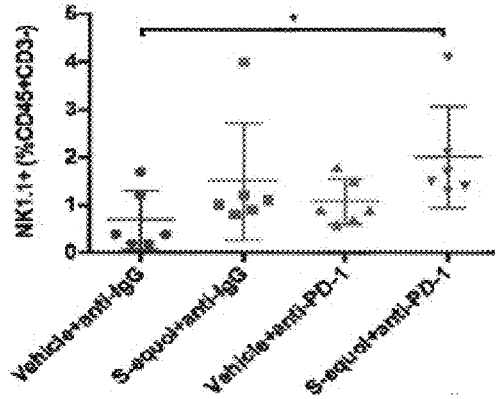
Figure 6:
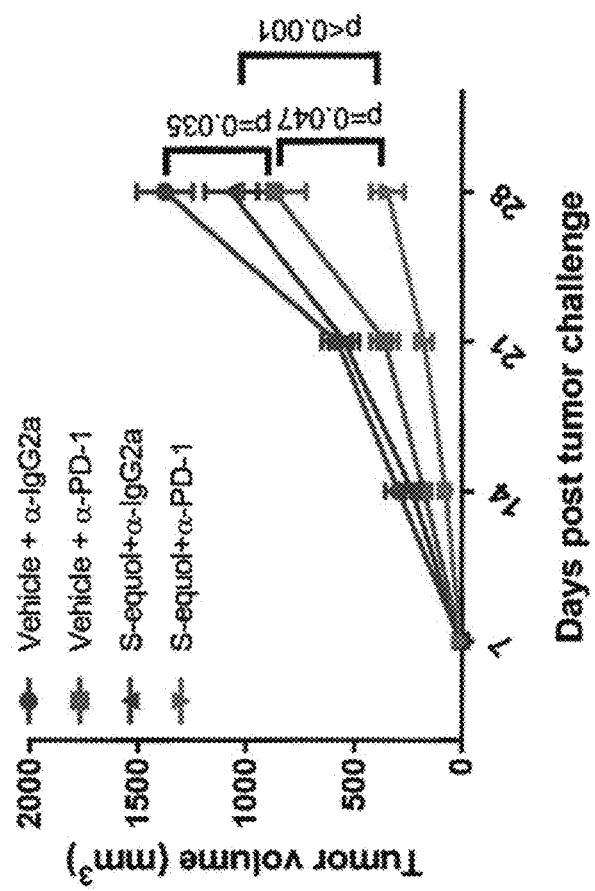
FIG. 6. Effect of S-equol in combination with an anti-PD-1 antibody on mice challenged with an E0771 mammary tumor cell line. Mice were administered anti-PD-1 antibody at 200 μg every 3 days and S-equol at 50 mg/kg per day.
Figure 7A:
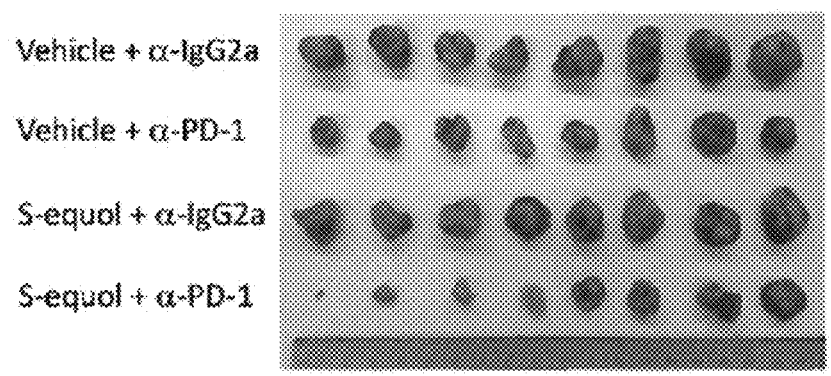
FIGS. 7A-7B. Effect of S-equol in combination with an anti-PD-1 antibody on mice challenged with an E0771 mammary tumor cell line.
Figure 7B:
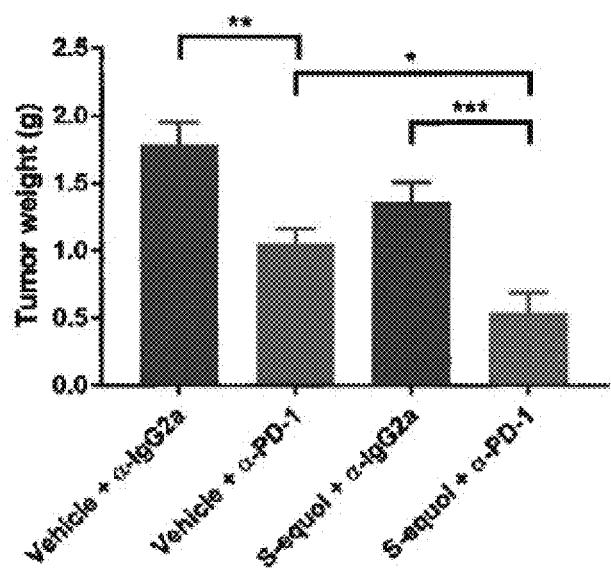

The following three murine mammary tumor lines were tested to determine the effects of a PD-1 inhibitor, S-equol and a combination of the two therapies on tumor growth: (1) E0771 (B6 background), (2) AT-3 (B6 background), and (3) 4T1 (BalbC background). This experimental design includes four arms (using AT-3 as an example): (1) controls, (2) αPD-1, (3) S-equol, and (4) αPD-1+S-equol (FIG. 3) by injecting into mice 2×10$^5$ cells subcutaneously into the 4$^{th}$ mammary gland fat pad. Antibodies were administered (α-PD-1: 200 μg/mice by i.p. injection every 3 days and S-equol was administered at 50 mg/kg/day by oral gavage. Treatment began 7 day after tumor challenge. Tumor growth trajectories were compared within treated mice using a repeated measures linear mixed model. The primary outcome was the logarithm of the tumor size, and the test statistic is the treatment×time interaction. Tumors were measured about 10 times. The number of recipient mice use used in the studies (n=8 per group) was based on the above study. Results (FIGS. 4-7) from this experiment demonstrate the ability of S-equol to boost anticancer immunotherapy.

Example 5

In addition to measurements of tumor size and weight in each arm, immunophenotyping was performed to gain more mechanistic insight into the antitumor effects of mono- and combinational therapies. Tumors, spleens, and draining lymph nodes were harvested and weighed. Anti-coagulated blood was collected by cardiac puncture. Tumors were paraffin-embedded for immunohistochemistry and snap-frozen for mRNA and protein analysis by Luminex. Flow cytometry was used (for phenotype/functions) and ViCell (for quantification) to analyze immune cells from tumor infiltrates, tumor-draining lymph nodes, and spleens. Analyses include CD3$^+$ total T cells and CD4$^+$ and CD8$^+$ T cell subsets; effector function (e.g., IFN-γ, TNF-α, IL-2, perforin, CD107a); activation (e.g., CD69, CD44, CD62L); and exhaustion (e.g., PD-1, Tim3, Lag3). Antigen-presenting cells (CD11b$^+$CD1c$^-$ monocyte/macrophages, CD11b$^+$CD11c+ dendritic cells), NK1.1$^+$ NKp46$^+$ NK cells, regulatory T cells (Treg, CD3$^+$CD4$^+$CD25$^{hi}$Foxp3$^+$), and myeloid-derived suppressor cells (MDSC, CD11b$^+$Gr-1$^{hi}$) were also analyzed. CD8$^+$ T cell receptor diversity were assessed with a commercial kit (Adaptive Biotechnologies). Local cell proliferation was also tested with Ki67 and BrdU stain.

Example 6

Figure 8:
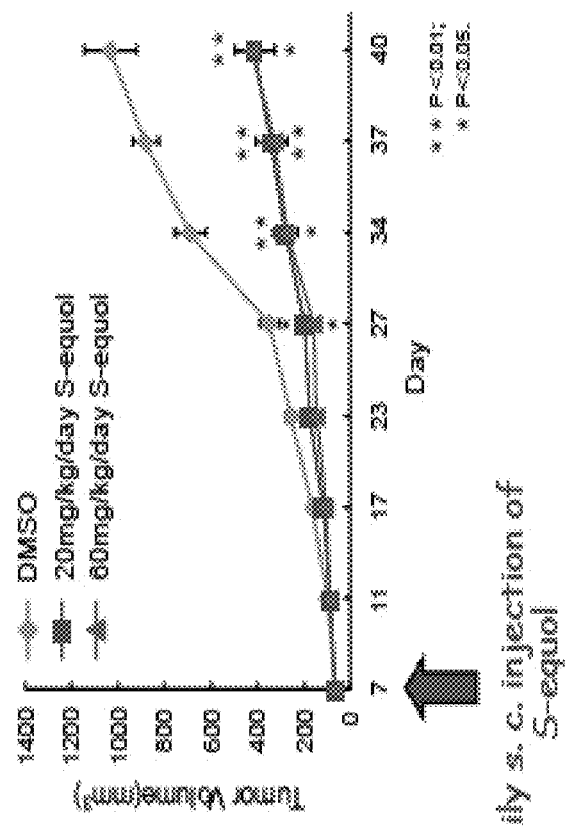
FIG. 8. S-equol inhibits tumor growth in vivo.
Figure 15A:
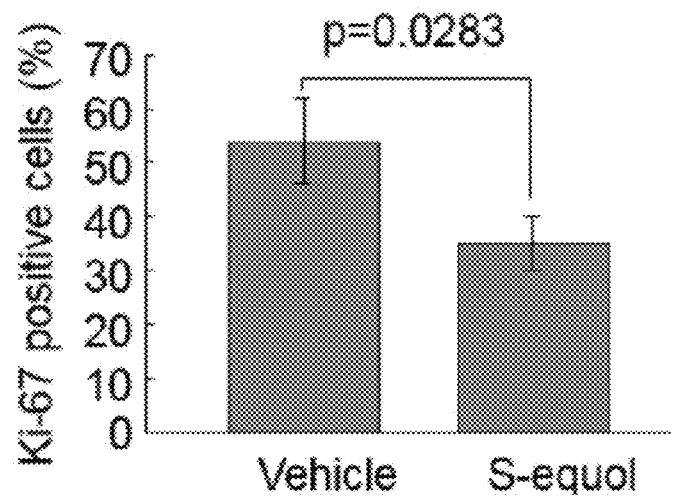
FIGS. 15A-15B. S-equol reduces the growth of TNBC cells in a xenograft mouse model.
Figure 15B:
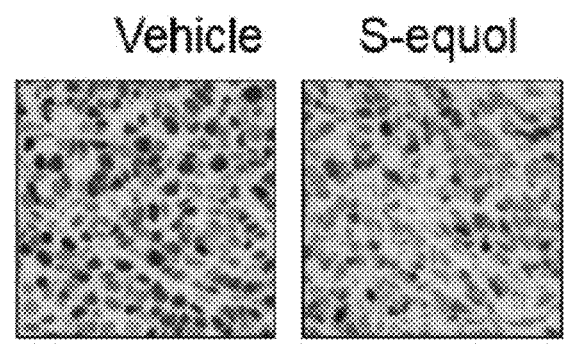
Figure 16A:
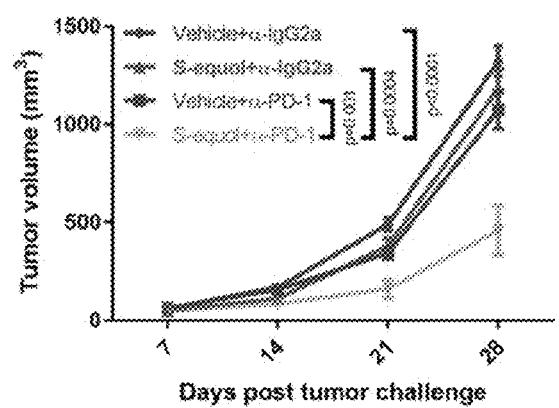
FIGS. 16A-16C. S-equol and/or α-PD-1 treatment with EMT6 mammary tumors. Mice were injected with $3 \times 10^5$ EMT6 cells. α-PD-1 was administered at 200 μg/mouse, intraperitoneally every 3 days and S-equol was administered at 50 mg/kg/day by oral gavage daily.
Figure 16B:
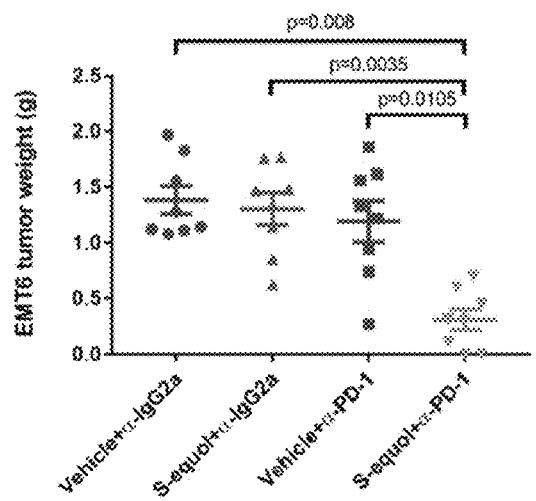
Figure 16C:
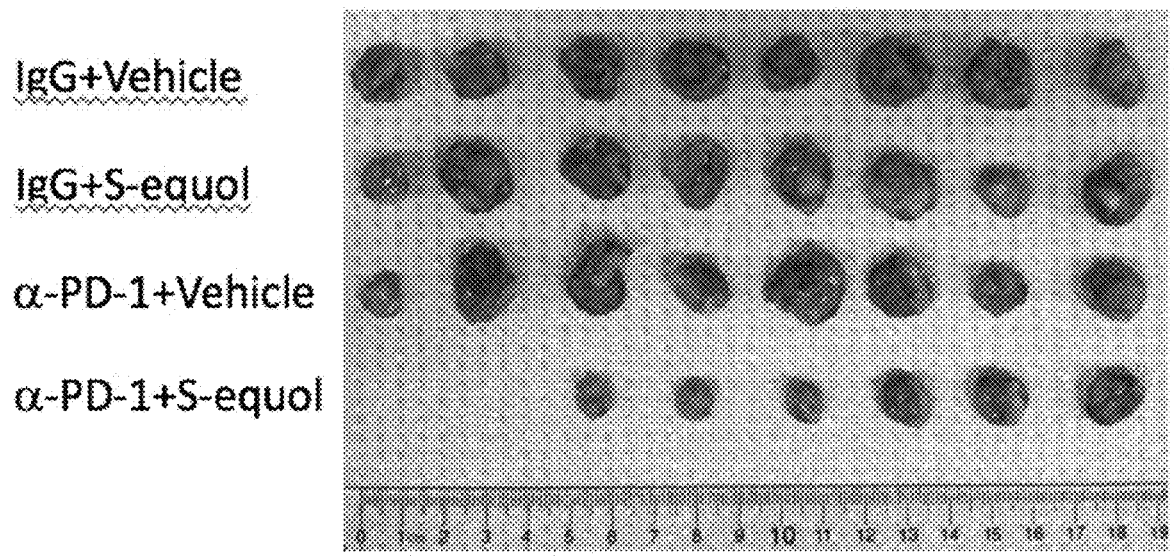
Figure 17A:
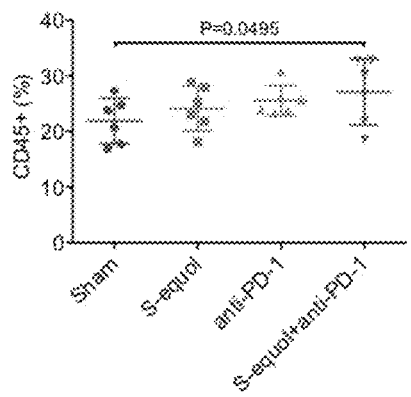
FIGS. 17A-17H. Expression of markers on EMT6 tumor cells after treatment.
Figure 17B:
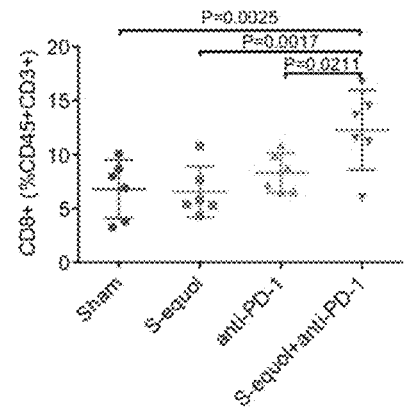
Figure 17C:
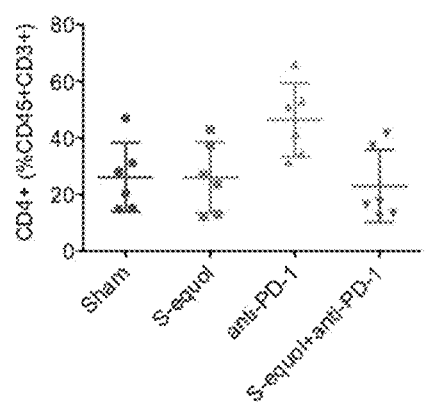
Figure 17D:
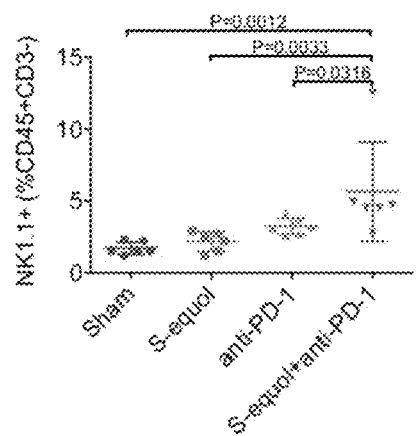
Figure 17E:
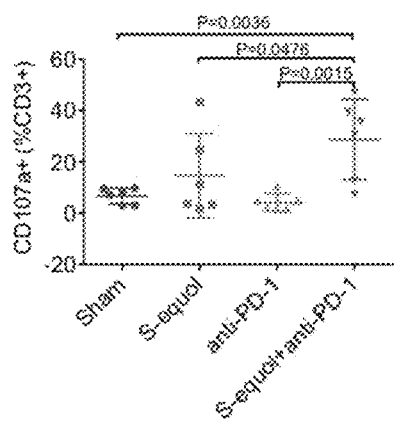
Figure 17F:
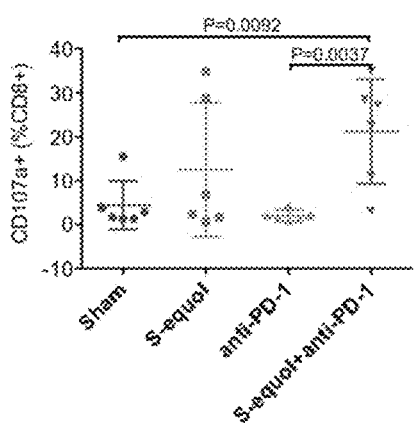
Figure 17G:
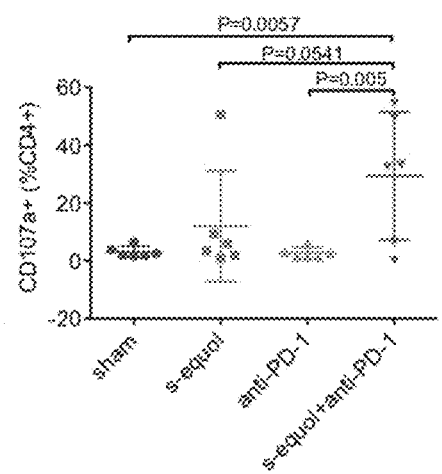
Figure 17H:
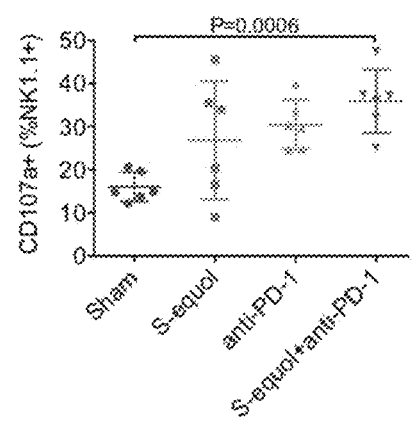
Figure 18A:
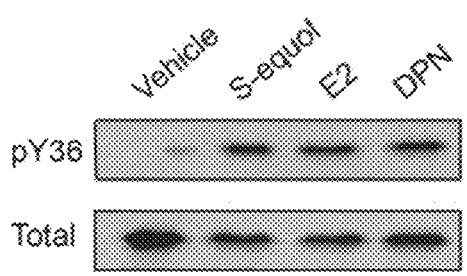
FIGS. 18A-18D. S-equol stimulates pY36 and inhibits tumor growth in vivo.
Figure 18B:
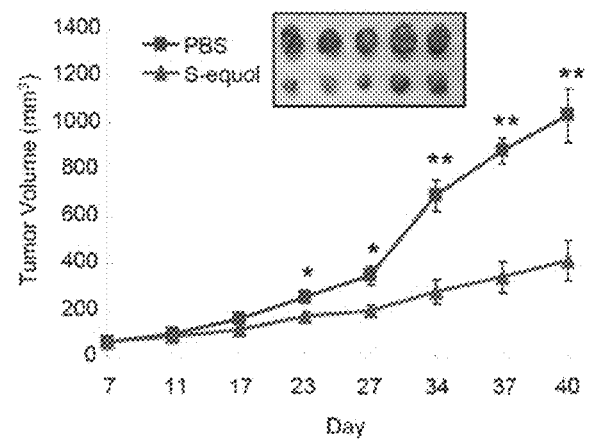
Figure 18C:
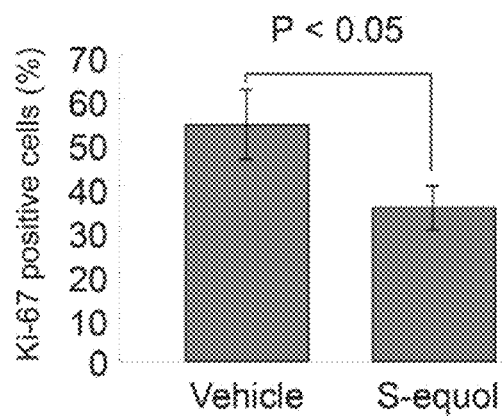
Figure 18D:
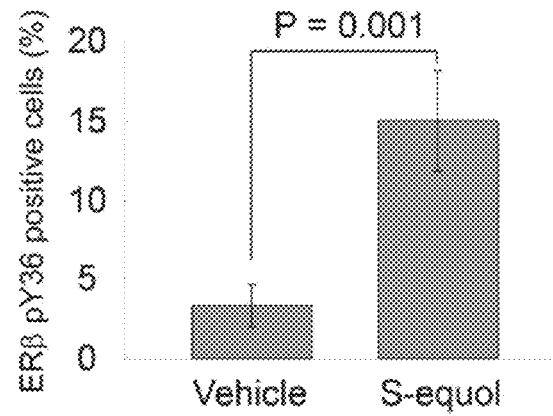

Further work in a preclinical animal model supports the notion of using S-equol to treat TNBC breast cancer. In immunocompromised mouse xenograft experiments, which used MDA-MB-231, a human TNBC breast cancer cell line, growth of tumors was suppressed by 60% with S-equol treatment compared to control. 5×10$^6$ MDA-MB-231 cells were injected orthotopically into mammary gland fat pads of 6 week-old female athymic nude mice (Harlan). When the tumor masses reached 50 to 80 mm$^3$ (about one week after the inoculation), the mice were given daily subcutaneous injections of S-equol (20 or 60 mg/kg per day) or PBS as a vehicle control. Tumor development was followed by caliper measurements along two orthogonal axes: length (L) and width (W) and volume (V) was estimated by the formula V=[L×(W$^2$)]/2. Xenograft tumors harvested from mice were fixed in 10% neutral-buffered formalin, dehydrated, embedded in paraffin, and sectioned at 3 μm thickness. Representative tumor sections from vehicle control and S-equol-treated mice were tested for Ki-67 expression to assess cell proliferation, and for ERβ pY36. Statistical significance in the experiments was assessed by two-tailed Student's t test. In all assays, p<0.05 was considered statistically significant. The results of these experiments are shown in FIGS. 8 and 15. See, Yuan et al. 2016 listed below, which is incorporated by reference herein for all purposes.

Example 7

Figure 13:
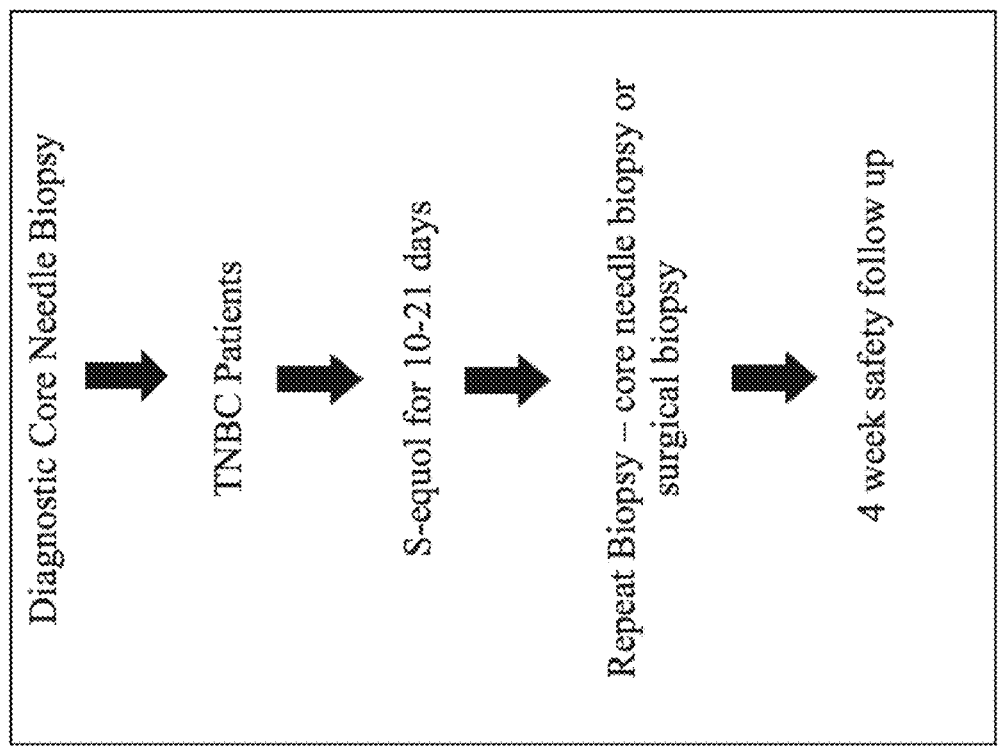
FIG. 13. Schematic for human clinical trial with S-equol.
Figure 14A:
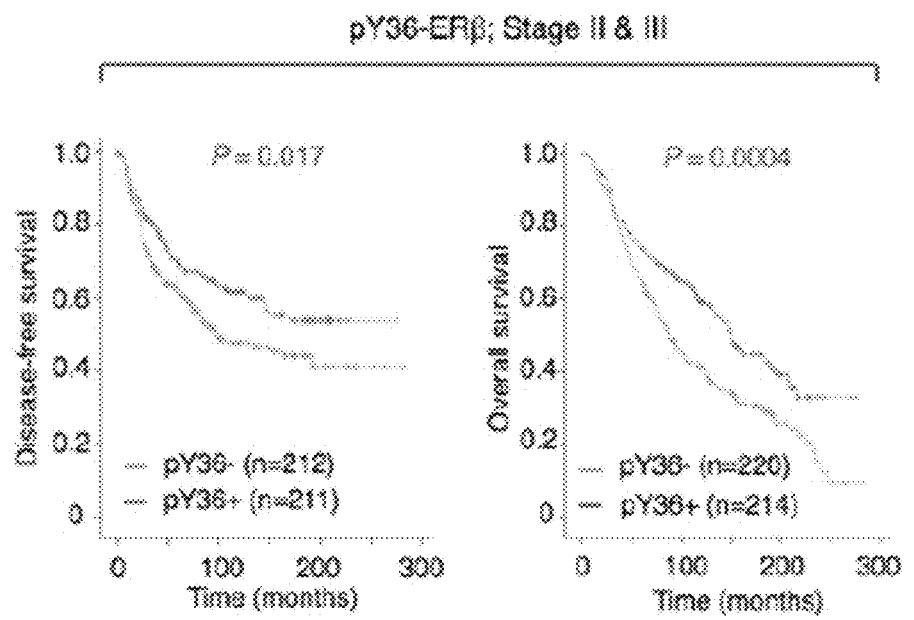
FIGS. 14A-14B. Association of pY36 with disease outcomes in breast cancer.
Figure 14B:
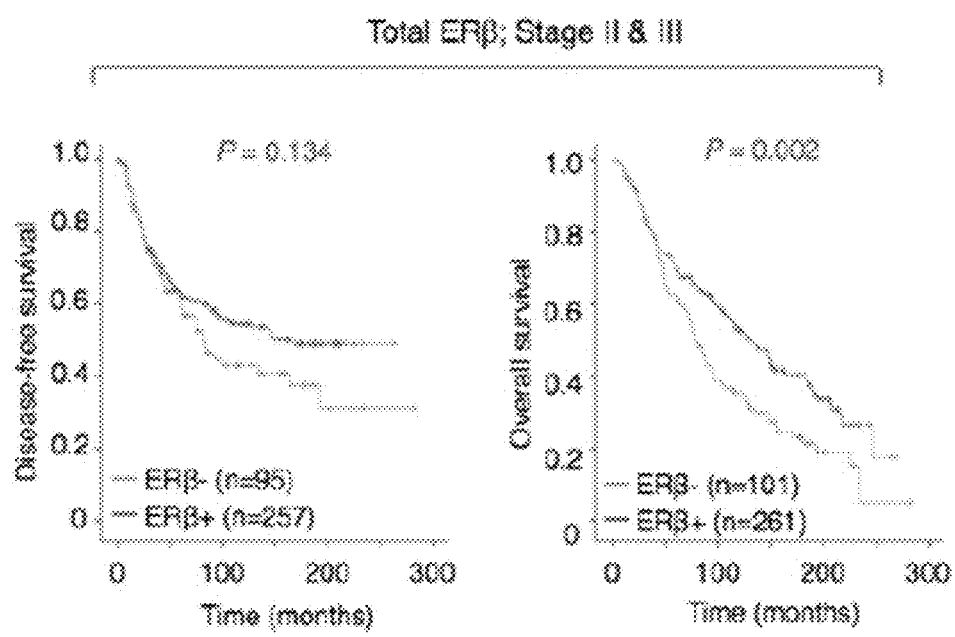

A pilot biomarker clinical study was performed in 20 subjects with documented TNBC to determine the effect of the ERβ agonist S-equol on Ki67 an indicator of tumor cell proliferation. Tumor cell proliferation was measured by immunohistological staining for Ki-67. See, FIG. 13 for the outline of the protocol. Ki-67 is encoded by the gene MKI67 gene and is required to maintain individual mitotic chromosomes dispersed in the cytoplasm following nuclear envelope disassembly. Measuring the fraction of Ki-67-positive cells in a tumor is known to be a reliable parameter for assessing cancer patient prognosis. Subjects with TNBC are known to have very high levels of Ki67.

Patients enrolled in the study received a history, physical, laboratory assessment, radiological imaging, and diagnostic biopsies. Immunohistochemistry (IHC) of Ki67 (proliferation marker), total ERβ, and pY36-ERβ (phosphorylated ERβ), B7H1 (also known as PDL-1) and BRCA1 (breast cancer 1, early onset) were conducted using core needle biopsy tissue samples prior to treatment. Patients were given oral S-equol 50 mg, twice daily for approximately two weeks (10-21 days) prior to the scheduled oncologic surgeries or start of primary systemic therapy. Tumor samples were obtained from the surgery or the two-week repeat core needle biopsy. Post-treatment IHC evaluation of Ki67, total ERβ, phosphorylated ERβ (pY36) and BRCA1 were obtained. Ki67 reduction is a validated surrogate marker of both short and long term hormonal therapy efficacy in trials of human breast cancer and was compared pre- and post-treatment with S-equol. S-equol caused a measurable decrease in Ki67, indicating its efficacy in this tumor type. A c-DNA microarray platform was also used to discover downstream transcriptional targets of ERβ resulting from activation by S-equol.

Figure 9:
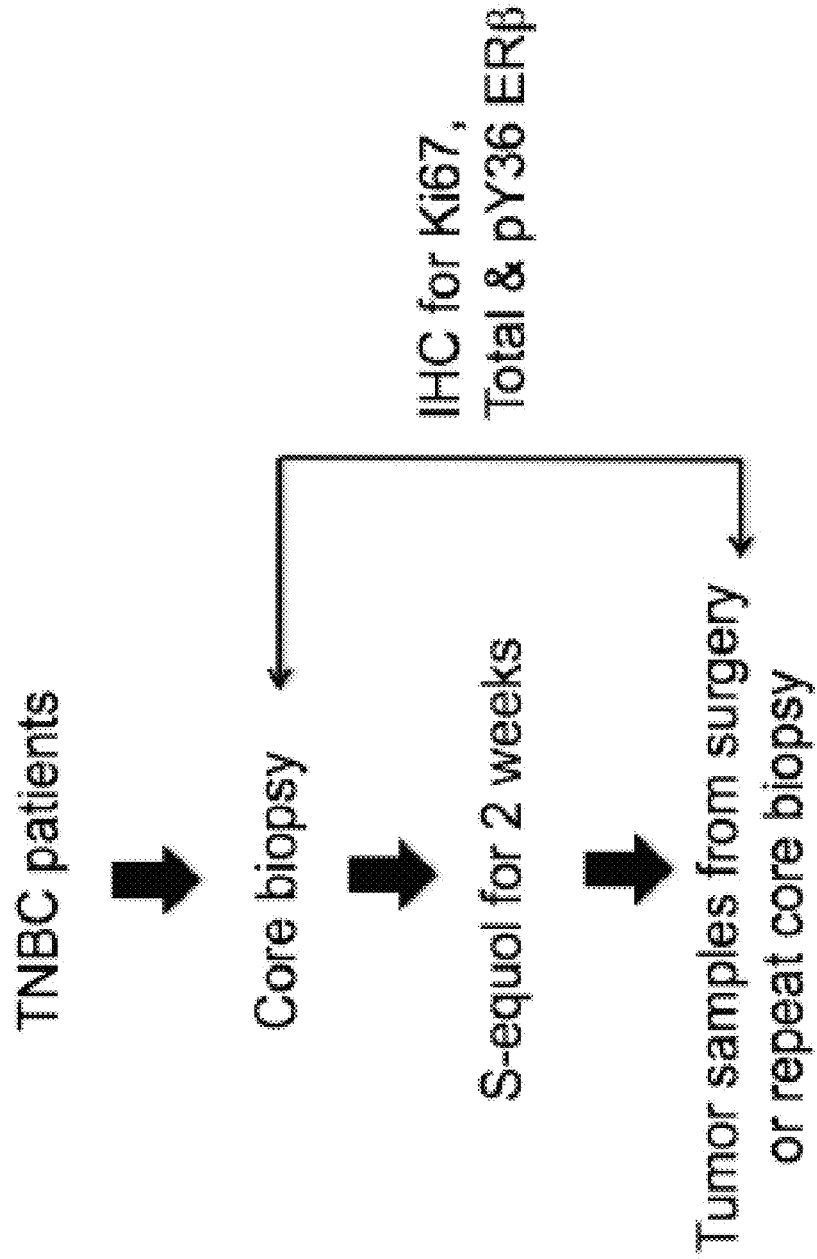
FIG. 9. Generalized protocol for treatment of patients with S-equol.
Figure 10:
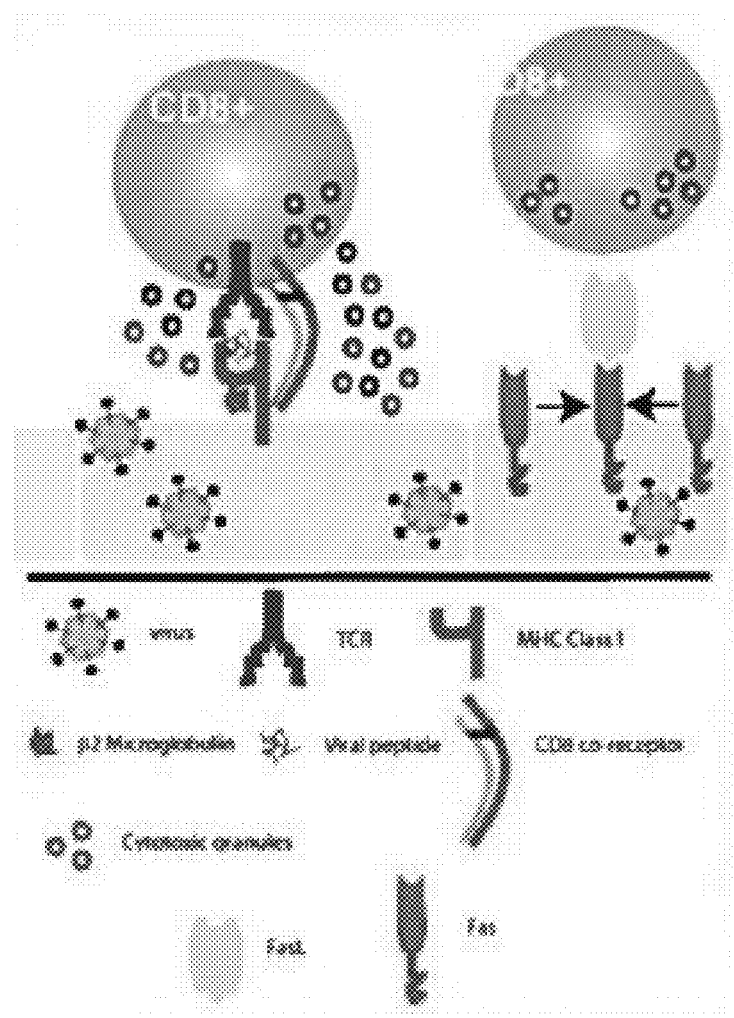
FIG. 10. Schematic depiction of the action of CD8+ cells.
Figure 11:
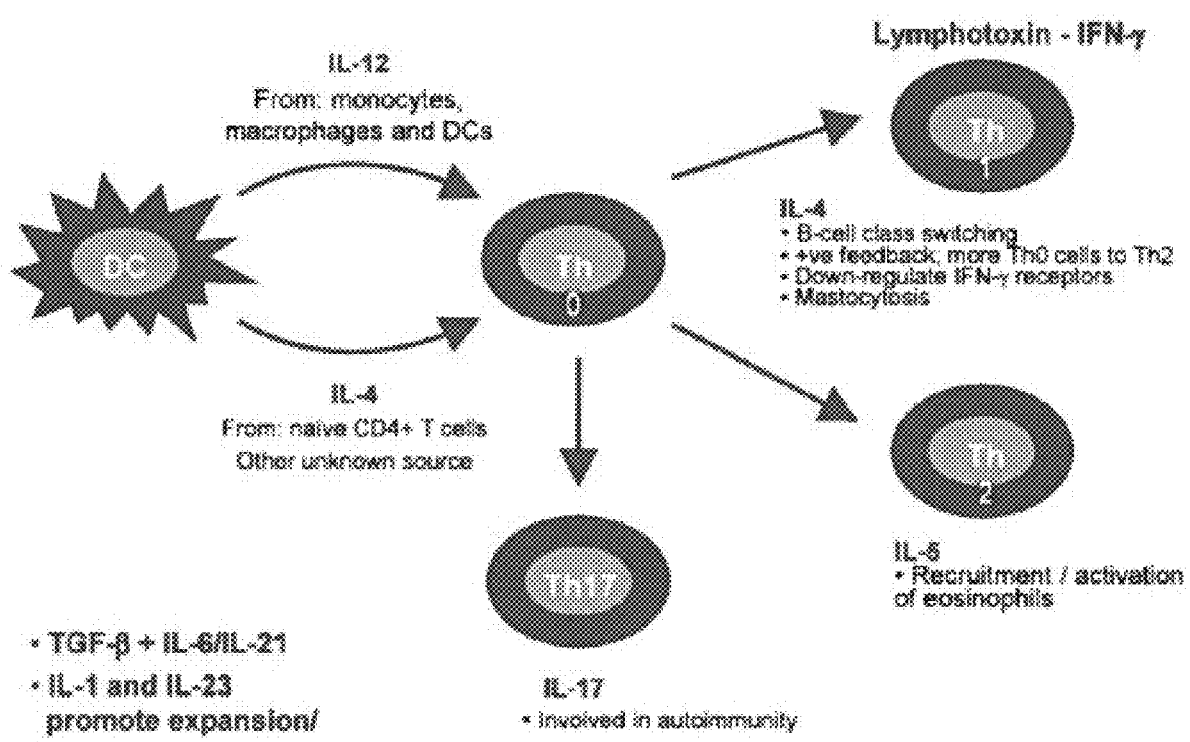
FIG. 11. Schematic depiction of the action of CD4+ cells.

Women eligible for the study had newly diagnosed, previously untreated, triple negative breast cancer, with an intact primary breast tumor of any size. All stages of the disease were eligible. They took S-equol during the time they underwent standard preoperative evaluation or pre-therapeutic work-up for advanced disease, such as staging procedures or central line placement. If primary surgery was performed, tissue leftover after standard diagnostic evaluation was used for the two-week biomarker assessment. If the patient did not have primary surgery at the end of the two-week S-equol treatment, a second set of 14-gauge core needle biopsies was obtained before the start of any standard systemic therapy. See, FIG. 9.

A standard procedure for acquiring core biopsy with a Bard 14-gauge needle was utilized for determining TNBC prior to enrollment. Whenever possible, the tumor tissues used for IHC analyses were acquired at the same time as the diagnostic core biopsy. The tissue samples were sent for staining of total and pY36 ERβ and Ki67, and analyzed. Testing for ERα, PR, and HER-2 was performed using validated methods. TNBC tumors were defined as less than 5% nuclear staining of carcinoma cells for ERα and PR and either 0, 1, or 2+ staining for HER-2 by IHC. Whole-Genome DASL HT platform from Illumina, which is designed for gene expression profiling with extremely low input of RNA (50 pg), was used to interrogate paired FFPE tissue obtained before and after exposure to S-equol.

Figure 12:
FIG. 12. Results from pilot clinical study (Example 7 below).

Statistical analysis was conducted which showed that ERβ-expressing TNBC responds to S-equol as manifested by measurable decline in Ki67. The primary analysis estimated the geometric mean change of the Ki67 expression from baseline to two weeks. This was performed using a one-sample t-test of the pre/post differences in the log-transformed data, and summarized by the 95% confidence interval. According to the IMPACT trial, the changes in the geometric mean of Ki67 expression after two weeks were −76, −59.5, and −63.9% for the anastrazole, tamoxifen, and combination groups respectively, with a standard deviation of approximately 1.0 on the log-scale. This implies effect sizes of 1.0 to 1.5 and a power >90% for testing for a decrease in Ki67 expression with two-sided $\alpha=0.05$ and a sample size of at least 45 patients accounting for variation in accrual and potential drop out. All computations were performed with SAS v9.2+(Cary, NC) or R v2.15+(Vienna, Austria). 20 patients enrolled and completed the study. 17 patients had evaluable pre- and post-treatment samples. Of these 17 evaluable patients, 4 patients had greater than 30% reduction in Ki-67, one patient had greater than 20% reduction, and 7 patients had 0-20% reduction (5 patients had no reduction in Ki-67). See, FIG. 12.

Example 8

A follow-up clinical study enrolls 25 newly diagnosed TNBC patients, and patients are treated and assessed as discussed in Example 7, except that the dose of S-equol is increased to 150 mg twice daily. Treatment with S-equol is for 10-21 days. Ki67 is analyzed as described in Example 7.

REFERENCES

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, documents, manuscripts and scientific literature cited herein are hereby incorporated by reference.

Altin, J. G. and Sloan, E. K. The role of CD45 and CD45-associated molecules in T cell activation. *Immunol. Cell Biol.* 75(5):430-435 (1997).

Baum M., Buzdar A. U., Cuzick J., et al. Anastrozole alone or in combination with tamoxifen versus tamoxifen alone for adjuvant treatment of postmenopausal women with early breast cancer: first results of the ATAC randomized trial. *Lancet.* 359: 2131-2139, (2002).

Beelen K., Zwart W., Linn S. C. Can predictive biomarkers in breast cancer guide adjuvant endocrine therapy? *Nat Rev Clin Oncol.* 9: 529-541, (2012).

Brahmer, J. R. et al. Safety and activity of anti-PD-L 1 antibody in patients with advanced cancer. *N Engl J Med* 366, 2455-2465, doi:10.1056/NEJMoal200694 (2012).

Brower, V. Checkpoint blockade immunotherapy for cancer comes of age. *J Natl Cancer Inst* 107, doi: 10.1093/jnci/djv069 (2015).

Chen, L. & Flies, D. B. Molecular mechanisms of T cell co-stimulation and co-inhibition. *Nat Rev Immunol* 13, 227-242, doi:10.1038/nri3405 (2013).

Chia, K. & Tutt, A. Triple-negative breast cancer: An update. *Adv Breast Cancer* 4, 75-80, (2007).

Cho, J. L., Allanson, M. & Reeve, V. E. Oestrogen receptor-beta signalling protects against transplanted skin tumour growth in the mouse. *Photochem Photobiol Sci* 9, 608-614, doi: 10.1039/b9pp00168a (2010).

Clarke R., Liu M., Bouker K. B., et al. Antiestrogen resistance in breast cancer and the role of estrogen receptor signaling. *Oncogene.* 22: 7316-7339, (2003).

Cleator, S., Heller, W. & Coombes, R. C. Triple-negative breast cancer: therapeutic options. *Lancet Oncol.* 8, 235-244, (2007).

Coates et al. "Tailoring therapies—improving the management of early breast cancer: St. Gallen International Expert Consensus on the Primary Therapy of Early Breast Cancer 2015,"*Annals of Oncology* 26(8):1533-46, (2015)

Curiel, T. J. et al. Blockade of B7-H1 improves myeloid dendritic cell-mediated antitumor immunity. *Nat Med* 9, 562-567, doi:10.1038/nm863 (2003).

Davies C., Pan H., Godwin J., et al. Long-term effects of continuing adjuvant tamoxifen to 10 years versus stopping at 5 years after diagnosis of estrogen receptor-positive breast cancer: ATLAS, a randomized trial. *Lancet.* 381: 805-816, 2013.

Dawood, S. & Rugo, H. S. Targeting the host immune system: PD-1 and PD-L 1 antibodies and breast cancer. *Curr Opin Support Palliat Care* 10, 336-342, doi: 10.1097/SPC.0000000000000243 (2016).

Dent, R. et al. Triple-negative breast cancer: clinical features and patterns of recurrence. *Clin Cancer Res.* 13, 4429-4434 (2007).

Deroo B. J., Korach K. S. Estrogen receptors and human disease. *J Clin Invest.* 116: 561-570, (2006).

Deroo B. J., Buensuceso A. V. Minireview: Estrogen receptor-beta: mechanistic insights from recent studies. *Mol Endocrinol.* 24: 1703-1714, (2010).

Diaz, L. K., Cryns, V. L., Symmans, W. F. & Sneige, N. Triple negative breast carcinoma and the basal phenotype: From expression profiling to clinical practice. *Advances in Anatomic Pathology* 14, 419-430 (2007).

Dirix, L. Y., Takacs, I. & Nikolinakos, P. e. a. Avelumab (MSB0010718C), an anti-PD-L1 antibody, in patients with locally advanced or metastatic breast cancer: A phase 1b JAVELIN solid tumor trial. 2015 San Antonio Breast Cancer Symposium Abstract S1-04, (2015).

Emens, L. A., Braiteh, F. S. & Cassier, P. e. a. Inhibition of PD-L 1 by MPDL3280A leads to clinical activity in patients with metastatic triple-negative breast cancer (TNBC). The American Association for Cancer Research Annual Meeting Abstract 2859, (2015).

Gerson, R., Alban, F., Villalobos, A. & Serrano, A. Recurrence and survival rates in early breast cancer cases with triple negative immunophenotype. *Gae Med Mex* 144, 27-34, (2008).

Gonzalez-Angulo, A. M. Advances in triple receptor-negative breast cancer. *Clin Adv Hematol Oncol* 5, 956-957 (2007).

Goss P. E., Ingle J. N., Martino S., et al. Randomized trial of letrozole following tamoxifen as extended adjuvant therapy in receptor-positive breast cancer: updated findings from NCIC CTG MA.17. *J Natl Cancer Inst.* 97: 1262-1271, (2005).

Haffty, B. G. et al. Locoregional relapse and distant metastasis in conservatively managed triple negative early-stage breast cancer. *J Clin Oncol.* 24, 5652-5657 (2006).

Harris H. A. Estrogen receptor-beta: recent lessons from in vivo studies. *Mol Endocrinol.* 21: 1-13, (2007).

Hartman J., Strom A., Gustafssom J. A. Estrogen receptor beta in breast cancer—diagnostic and therapeutic implications. *Steroids.* 74: 635-641, (2009).

Heldring N., Pike A., Anderrson S., et al. Estrogen receptors: how do they signal and what are their targets. *Physiol Rev.* 87: 905-931, (2007).

Honma N., Hori R., Iwase T. et al: Clinical importance of estrogen receptor-beta evaluation in breast cancer patients treated with adjuvant tamoxifen therapy. *J Clin Oncol.* 26: 3727-3734, (2008).

Irvin, W. J. J. & Carey, L. A. What is triple-negative breast cancer? *Eur J Cancer.* 44, 2799-2805, (2008).

Jackson R. L., Greiwe J. S., Schwen R. J. Emerging evidence of the health benefits of S-equol, an estrogen receptor beta agonist. *Nutr Rev.* 69: 432-448, (2011a).

Jackson R. L., Greiwe J. S., Schwen R. J. Single-dose and steady-state pharmacokinetic studies of S-equol, a potent nonhormonal, estrogen receptor beta-agonist being developed for the treatment of menopausal symptoms. *Menopause,* 18 185-193, (2011b)

Jenks et al., A pilot study on the effects of S-equol compared to soy isoflavones on menopausal hot flash frequency, *Journal of Women's Health,* 21 (2012) 674-682, (2002).

Kang, S. P., Martel, M. & Harris, L. N. Triple negative breast cancer: current understanding of biology and treatment options. *Curr Opin Obstet Gynecol.* 20, 40-46, (2008).

Kaplan, H. G. & Malmgren, J. A. Impact of triple negative phenotype on breast cancer prognosis. *Breast Journal* 14, 456-463, (2008).

Katzenellenbogen B., Katzenellenbogen J. Estrogen receptor transcription and transactivation: Estrogen receptor alpha and estrogen receptor beta: regulation by selective estrogen receptor modulators and importance in breast cancer. *Breast Cancer Res.* 2: 335-344, (2000).

Kittaneh et al. "Molecular profiling for breast cancer: A comprehensive review," *Biomark Cancer* 5:61-70, (2013).

Krege, J. H. et al. Generation and reproductive phenotypes of mice lacking estrogen receptor beta. *Proc Natl Acad Sci USA* 95, 15677-15682, (1998).

Lin, P. Y. et al. B7-H1-dependent sex-related differences in tumor immunity and immunotherapy responses. *J Immunol* 185, 2747-2753, doi:10.4049/jimmunol.1000496 (2010).

Marotti, J. D., Collins, L. C., Hu, R. & Tamimi, R. M. Estrogen receptor-beta expression in invasive breast cancer in relation to molecular phenotype: results from the Nurses' Health Study. *Modern Pathology* 23, 197-204, doi:10.1038/modpathol.2009. 158, (2010).

McDonnell D., Norris J.: Connections and regulation of the human estrogen receptor. *Science.* 296: 1642-1644, (2002).

Mellman, I., Coukos, G. & Dranoff, G. Cancer immunotherapy comes of age. *Nature* 480, 480-489, doi:10.1038/nature10673 (2011).

Murphy L. C., Watson P. H. Is oestrogen receptor-beta a predictor of endocrine therapy responsiveness in human breast cancer? *Endocr Relat Cancer.* 13: 327-334, (2006).

Nanda, R. et al. Pembrolizumab in patients with advanced triple-negative breast cancer: Phase 1b KEYNOTE-012 Study. *J Clin Oncol* 34, 2460-2467, doi:10.1200/JC0.2015.64.8931 (2016).

Pardoll, D. & Drake, C. Immunotherapy earns its spot in the ranks of cancer therapy. *J Exp Med* 209, 201-209, doi: 10.1084/jem.20112275 (2012).

Pardoll, D. M. The blockade of immune checkpoints in cancer immunotherapy. *Nat Rev Cancer* 12, 252-264, doi: 10.1038/nrc3239 (2012).

Pfefferle, A. D. et al. Transcriptomic classification of genetically engineered mouse models of breast cancer identifies human subtype counterparts. *Genome Biol* 14, R125, doi:10.1186/gb-2013-14-11-r125 (2013).

Reese, J. M. et al. ERβ: characterization, prognosis, and evaluation of treatment strategies in ER alpha positive and −negative breast cancer. *BMC Cancer* 14, 749, doi: 10.1186/1471-2407-14-749 (2014).

Reis-Filho, J. S. & Tutt, A. N. J. Triple negative tumours: A critical review. *Histopathology* 52, 108-118, (2008).

Ribas, A. and Wolchok, J. D. Cancer immunotherapy using checkpoint blockade. *Science* 359:1350-1355, (2018).

Rugo, H. S. et al. Preliminary efficacy and safety of pembrolizumab (MK-3475) in patients with PD-L1-positive, estrogen receptor-positive (ER+)/HER2-negative advanced breast cancer enrolled in KEYNOTE-028. 2015 *San Antonio Breast Cancer Symposium Abstract S5-07* (2015).

Sachs, J. R. et al. Optimal dosing for targeted therapies in oncology: drug development cases leading by example. Clin. Cancer Res. 22(6):OF1-7 (2016).

Sahin, U. and Tureci, O. Personalized vaccines for cancer immunotherapy. *Science* 359:1355-1356, (2018).

Santen R. J., Brodie H., Simpson E. R., et al. History of aromatase: saga of an important biological mediator and therapeutic target. *Endocr Rev.* 30: 343-375, (2009).

Schwen, R. J., Greiwe, J. S., Schwen, R. J. Elucidation of the metabolic pathway of s-equol in rat, monkey and man. *Food Chemistry Toxicology.* 50: 2074-2083, (2012).

Setchell, K. D., Clerici C., Lephart E. D., et al. S-equol, a potent ligand for estrogen receptor beta, is the exclusive enantiomeric form of the soy isoflavone metabolite produced by human intestinal bacterial flora. *Am J Clini Nutr.* 81: 1072-1079, (2005).

Setchell, K. D. The clinical importance of the metabolite equol—a clue to the effectiveness of soy and its isoflavones. *Nature.* 132:3577-3584, (2002).

Shaaban A. M., Green A. R., Karthik S. Nuclear and cytoplasmic expression of ERbeta1, ERbeta2, and ERbeta5 identifies distinct prognostic outcome for breast cancer patients. *Clin Cancer Res.* 14: 5228-5235, (2008).

Sharma, P. & Allison, J. P. Immune checkpoint targeting in cancer therapy: toward combination strategies with curative potential. *Cell* 161, 205-214, doi:10.1016/j.cell.2015.03.030 (2015).

Shou J., Massarweh S., Osborne C. K., et al. Mechanisms of tamoxifen resistance: increased estrogen receptor-HER2/neu cross-talk in ER/HER2-positive breast cancer. *J Natl Cancer Inst.* 96: 926-935, 2004.

Smith I. E., Dowsett M., Ebbs S., et al. Neoadjuvant treatment of postmenopausal breast cancer with anastrozole, tamoxifen, or both in combination: The immediate preoperative anastrozole, tamoxifen, or combined with tamoxifen (IMPACT) multicenter double-blind randomized trial. *J Clini Onc.* 23: 5108-5116, (2005).

Thomas C., Gustafsson J. A. The different roles of ER subtypes in cancer biology and therapy. *Nat Rev Cancer.* 11: 597-608, (2011).

Topalian, S. L., Drake, C. G. & Pardoll, D. M. Immune checkpoint blockade: a common denominator approach to cancer therapy. *Cancer Cel* 27, 450-461, doi:10.1016/j.ccell.2015.03.001 (2015).

Topalian, S. L., Drake, C. G. & Pardall, D. M. Targeting the PD-1/B7-H1(PD-L1) pathway to activate anti-tumor immunity. *Curr Opin Immunol* 24, 207-212, doi:10.1016/j.coi.2011.12.009 (2012).

Urruticoechea A., Smith I., Dowsett M. Proliferation marker Ki-67 in early breast cancer. *Journal of Clinical Oncology* 23:7212-7220, (2005).

Usui et al., Effects of natural S-equol supplements on overweight or obesity and metabolic syndrome in the Japanese, based on sex and equol status, *Clinical endocrinology,* 78 365-372, (2013).

Yao et al., Potentiation of brain mitochondrial function by S-equol and R/S-equol estrogen receptor beta-selective phytoSERM treatments, *Brain Research,* 1514 128-141, (2013).

Yuan, B. et al. A phosphotyrosine switch determines the antitumor activity of ERbeta. *J Clin Invest* 124, 3378-3390, doi:10.1172/JCI74085 (2014).

Yuan B., Cheng L., Chiang H. C., et al. Mobilizing ERβ antitumor activity through a phosphotyrosine switch. *J Clini Invest.* 124(8):3378-90, (2014).

Yuan, B. et al. Tyrosine phosphorylation regulates ERbeta ubiquitination, protein turnover, and inhibition of breast cancer. *Oncotarget,* doi: 10.18632/oncotarget.10018 (2016).

Zhao et al., A select combination of clinically relevant phytoestrogens enhances estrogen receptor β-binding selectivity and neuroprotective activities in vitro and in vivo. *Neuroendocrinology,* 150(2):770-783, (2009).

The invention claimed is:

1. A method for treating triple-negative breast cancer, comprising administering to a patient diagnosed with triple-negative breast cancer a composition comprising equol and an anti-PD-1 antibody in a combination which is effective to reduce the size of a triple-negative breast cancer tumor in said patient, wherein said equol consists essentially of S-equol.

2. The method of claim 1, wherein 50-150 mg S-equol is administered.

3. The method of claim 1, wherein 50 mg+/−10% S-equol is administered.

4. The method of claim 1, wherein 150 mg+/−10% S-equol is administered.

5. The method of claim 1, wherein the S-equol is administered orally, intravenously, intraperitoneally, or subcutaneously.

6. The method of claim 1, wherein said patient is a human.

7. The method of claim 1, wherein the antibody is pembrolizumab.

8. The method of claim 1, wherein the S-equol is essentially free of genistein, daidzein, and/or IBS003569.

9. The method of claim 1, wherein genistein, daidzein, and/or IBS003569 are not co-administered with S-equol.

10. The method of claim 1, wherein the S-equol is essentially free of R-equol.

11. The method of claim 1, wherein the S-equol is produced chemically.

12. The method of claim 1, wherein the S-equol is administered once per day.

13. The method of claim 1, wherein the S-equol is administered twice per day.

14. The method of claim 1, wherein the S-equol is administered three times per day.

15. The method of claim 1, wherein the S-equol is administered four times per day.

16. The method of claim 1, wherein the anti-PD-1 antibody is administered at 2 mg/kg to 10 mg/kg.

17. The method of claim 1, wherein the anti-PD-1 antibody is administered intermittently every two weeks.

18. The method of claim 1, wherein the anti-PD-1 antibody is administered at 200 mg.

19. The method of claim 18, wherein the anti-PD-1 antibody is administered intermittently every three weeks.

* * * * *